(12) United States Patent
Wang et al.

(10) Patent No.: US 10,304,193 B1
(45) Date of Patent: May 28, 2019

(54) IMAGE SEGMENTATION AND OBJECT DETECTION USING FULLY CONVOLUTIONAL NEURAL NETWORK

(71) Applicant: 12 Sigma Technologies, San Diego, CA (US)

(72) Inventors: Yunzhi Wang, Oklahoma City, OK (US); Haichao Yu, Urbana, IL (US); Dashan Gao, San Diego, CA (US); Jiao Wang, San Diego, CA (US)

(73) Assignee: 12 Sigma Technologies, San Diego, CA (US)

( * ) Notice: Subject to any disclaimer, the term of this patent is extended or adjusted under 35 U.S.C. 154(b) by 0 days.

(21) Appl. No.: 16/104,449

(22) Filed: Aug. 17, 2018

(51) Int. Cl.
*G06K 9/62* (2006.01)
*G06T 7/11* (2017.01)
*G16H 30/20* (2018.01)
*G06N 3/08* (2006.01)
*G06T 7/00* (2017.01)

(52) U.S. Cl.
CPC ............ *G06T 7/11* (2017.01); *G06K 9/6232* (2013.01); *G06K 9/6257* (2013.01); *G06K 9/6262* (2013.01); *G06N 3/084* (2013.01); *G16H 30/20* (2018.01); *G06K 2209/05* (2013.01); *G06T 7/0012* (2013.01); *G06T 2207/10088* (2013.01); *G06T 2207/20081* (2013.01); *G06T 2207/20084* (2013.01); *G06T 2207/30081* (2013.01); *G06T 2207/30096* (2013.01)

(58) Field of Classification Search
CPC ................ G06K 9/0061; G06K 9/3233; G06T 2207/20081; G06T 2207/20084; G06T 7/11; G06T 3/4046
See application file for complete search history.

(56) References Cited

U.S. PATENT DOCUMENTS

2017/0200067 A1\* 7/2017 Zhou ........................ G06T 7/143
2018/0161986 A1\* 6/2018 Kee ........................ G06K 9/0064
2018/0285700 A1\* 10/2018 Stoop ........................ G06K 9/66

OTHER PUBLICATIONS

Abadi et al., *TensorFlow: A System for Large-Scale Machine Learning*, 12th USENIX Symposium on Operating Systems Design and Implementation, pp. 265-283 (Nov. 2-4, 2016) Savannah, GA.
(Continued)

*Primary Examiner* — Euengnan Yeh
(74) *Attorney, Agent, or Firm* — Brinks Gilson & Lione

(57) ABSTRACT

This disclosure relates to digital image segmentation, region of interest identification, and object recognition. This disclosure describes a method, a system, for image segmentation based on fully convolutional neural network including an expansion neural network and contraction neural network. The various convolutional and deconvolution layers of the neural networks are architected to include a coarse-to-fine residual learning module and learning paths, as well as a dense convolution module to extract auto context features and to facilitate fast, efficient, and accurate training of the neural networks capable of producing prediction masks of regions of interest. While the disclosed method and system are applicable for general image segmentation and object detection/identification, they are particularly suitable for organ, tissue, and lesion segmentation and detection in medical images.

21 Claims, 17 Drawing Sheets

(56) References Cited

OTHER PUBLICATIONS

Chen et al., *VoxResNet: Deep Voxelwise Residual Networks for Volumetric Brain Segmentation*, pp. 1-9, arXiv:1608.05895v1. Aug. 21, 2016.

Cheng et al., *Automatic magnetic resonance prostate segmentation by deep learning with holistically nested networks*, Journal of Medical Imaging, 4(4), 041302 (2017), doi: 10.1117/1.JMI.4.4. 041302, (published before this application Aug. 2018).

Dou et al., *3D deeply supervised network for automated segmentation of volumetric medical images*, Medical Image Analysis 41:40-54, 2017, (published before this application Aug. 2018).

Haider et al., *Combined T2-Weighted and Diffusion-Weighted MRI for Localization of Prostate Cancer*, AJR:189:323-328, Aug. 2007.

He et al., *Deep Residual Learning for Image Recognition*, https://arxiv.org, pp. 770-778 (2015), (published before this application Aug. 2018).

Kim et al., *Accurate Image Super-Resolution Using Very Deep Convolutional Networks*, pp. 1-9, (2016), (published before this application Aug. 2018).

Kitajima et al., *Prostate Cancer Detection With 3 T MRI: Comparison of Diffusion-Weighted Imaging and Dynamic Contrast-Enhanced MRI in Combination With T2-Weighted Imaging*, Journal of Magnetic Resonance Imaging 31:625-631 (2010), (published before this application Aug. 2018).

Kohl et al., *Adversarial Networks for the Detection of Aggressive Prostate Cancer*, pp. 1-8, (Under review as a conference paper at MICCAI 2017.) arXiv:1702.08014v1 Feb. 26, 2017.

Kozlowski et al., *Combined Diffusion-Weighted and Dynamic Contrast-Enhanced MRI for Prostate Cancer Diagnosis—Correlation With Biopsy and Histopathology*, Journal of Magnetic Resonance Imaging 24:108-113 (2006), (published before this application Aug. 2018).

Lee et al., *Deeply Supervised Nets*, Proceedings of the $18_{th}$ International Conference on Artificial Intelligence and Statistics (AISTATS), JMLR: W&CP vol. 38, 2015, San Diego, CA, USA, (published before this application Aug. 2018).

Litjens et al., *Computer-Aided Detection of Prostate Cancer in MRI* pp. 1083-1092, IEEE Transactions on Medical Imaging, 33:5, (May 2014).

Milletari et al., *V-Net: Fully Convolutional Neural Networks for Volumetric Medical Image Segmentation*, pp. 1-11, https://arXiv:1606. 04797v1. Jun. 15, 2016.

Ronneberger et al., *U-Net: Convolutional Networks for Biomedical Image Segmentation*, pp. 1-8 arXiv:1505.04597v1. May 18, 2015.

Long et al., *Fully Convolutional Networks for Semantic Segmentation*, CVPR2015 by Computer Vision Foundation (2015), (published before this application Aug. 2018).

Tsehay et al., *Convolutional neural network based deep-learning architecture for prostate cancer detection on multiparametric magnetic resonance images*, Proc. SPIE 10134, Medical Imaging 2017: Computer-Aided Diagnosis, 1013405 (Mar. 3, 2017); doi: 10.1117/12.2254423, Orlando, FL.

Wang et al., *Computer Aided-Diagnosis of Prostate Cancer on Multiparametric MRI: A Technical Review of Current Research*, Hindawi Publishing Corp., vol. 2014, pp. 1-12, Dec. 1, 2014 (http://dx.doi.org/10.1155/2014/789561).

Xu et al., *Deep Image Matting*, https://arxiv.org/abs/1703.03872, pp. 2970-2979, (2017), (published before this application Aug. 2018).

Yu et al., *Volumetric ConvNets with Mixed Residual Connections for Automated Prostate Segmentation from 3D MR Images*, Proceedings of the Thirty-First AAAI Conference on Artificial Intelligence pp. 66-72 (AAAI-17) (2017), (published before this application Aug. 2018).

Zhu et al.: *MRI based prostate cancer detection with high-level representation and hierarchical classification*, Medical Physics, pp. 1028-1039, 44 (3), Mar. 2017. https://doi.org/10.1002/mp.12116.

\* cited by examiner

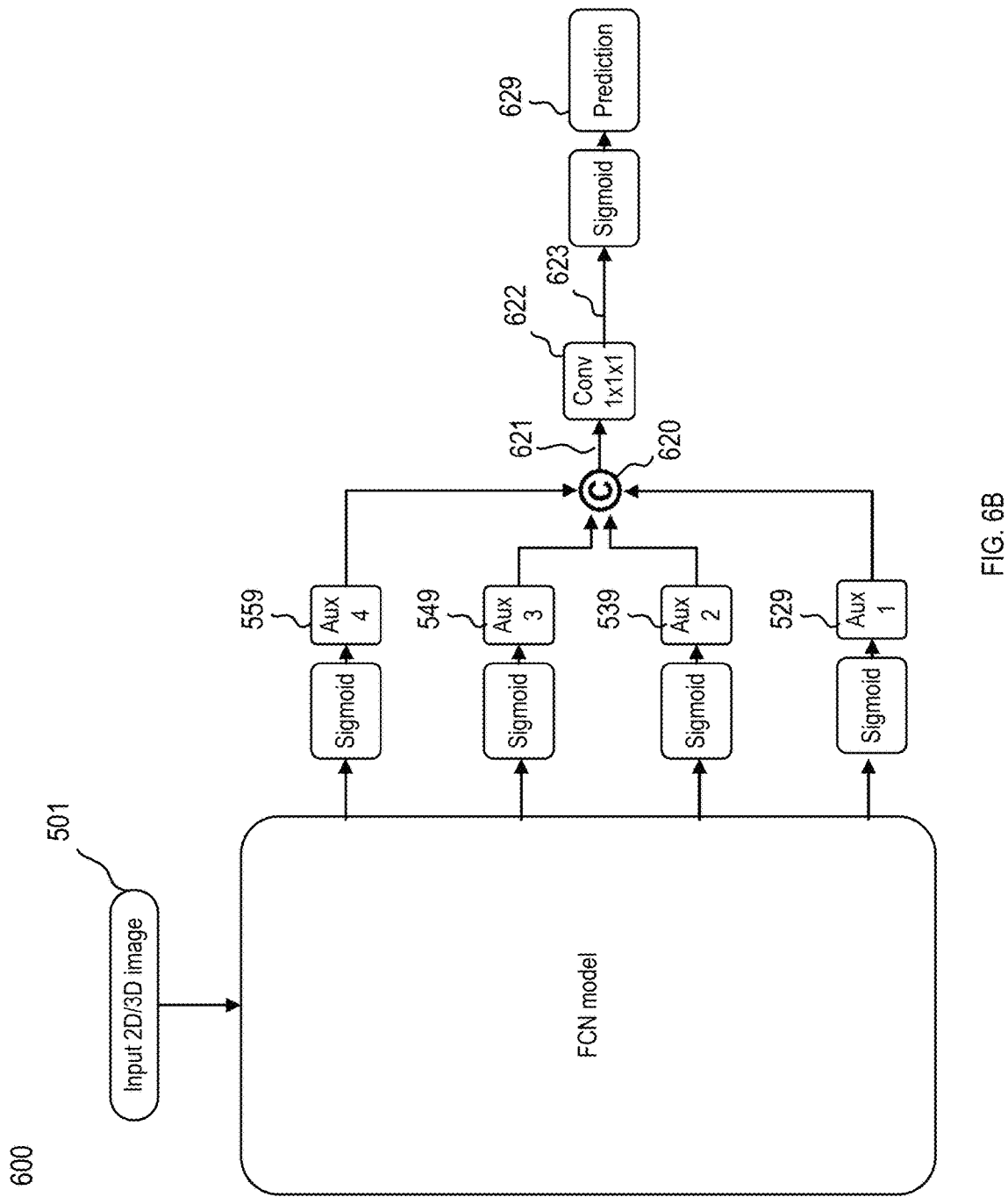

US 10,304,193 B1

IMAGE SEGMENTATION AND OBJECT DETECTION USING FULLY CONVOLUTIONAL NEURAL NETWORK

TECHNICAL FIELD

This disclosure relates generally to computer segmentation and object detection in digital images and particularly to segmentation of multi-dimensional and multi-channel medical images and to detection of lesions based on convolutional neural networks.

BACKGROUND

A digital image may contain one or more regions of interest (ROIs). In many applications, only image data contained within the one or more ROIs of a digital image may need to be retained for further processing and for information extraction by computers. Efficient and accurate identification of these ROIs thus constitutes a critical step in image processing applications, including but not limited to applications that handle high-volume and/or real-time digital images. Each ROI of a digital image may contain pixels forming patches with drastic variation in texture and pattern, making accurate and efficient identification of the boundary between these ROIs and the rest of the digital image a challenging task for a computer. In some imaging processing applications, an entire ROI or a subsection of an ROI may need to be further identified and classified. For example, in the field of computer-aided medical image analysis and diagnosis, an ROI in a medical image may correspond to a particular organ of a human body and the organ region of the image may need to be further processed to identify, e.g., lesions within the organ, and to determine the nature of the identified lesions.

SUMMARY

This disclosure is directed to an enhanced convolutional neural network including a contraction neural network and an expansion neural network. These neural networks are connected in tandem and are enhanced using a coarse-to-fine architecture and densely connected convolutional module to extract auto-context features for more accurate and more efficient segmentation and object detection in digital images.

The present disclosure describes a method for image segmentation. The method includes receiving, by a computer comprising a memory storing instructions and a processor in communication with the memory, a set of training images labeled with a corresponding set of ground truth segmentation masks. The method includes establishing, by the computer, a fully convolutional neural network comprising a multi-layer contraction convolutional neural network and an expansion convolutional neural network connected in tandem. The method includes iteratively training, by the computer, the full convolution neural network in an end-to-end manner using the set of training images and the corresponding set of ground truth segmentation masks by down-sampling, by the computer, a training image of the set of training images through the multi-layer contraction convolutional neural network to generate an intermediate feature map, wherein a resolution of the intermediate feature map is lower than a resolution of the training image; up-sampling, by the computer, the intermediate feature map through the multi-layer expansion convolutional neural network to generate a first feature map and a second feature map, wherein a resolution of the second feature map is larger than the resolution of the first feature map; generating, by the computer based on the first feature map and the second feature map, a predictive segmentation mask for the training image; generating, by the computer based on a loss function, an end loss based on a difference between the predictive segmentation mask and a ground truth segmentation mask corresponding to the training image; back-propagating, by the computer, the end loss through the full convolutional neural network; and minimizing, by the computer, the end loss by adjusting a set of training parameters of the fully convolutional neural network using gradient descent.

The present disclosure also describes a computer image segmentation system for digital images. The computer image segmentation system for digital images includes a communication interface circuitry; a database; a predictive model repository; and a processing circuitry in communication with the database and the predictive model repository. The processing circuitry configured to: receive a set of training images labeled with a corresponding set of ground truth segmentation masks. The processing circuitry configured to establish a fully convolutional neural network comprising a multi-layer contraction convolutional neural network and an expansion convolutional neural network connected in tandem. The processing circuitry configured to iteratively train the full convolution neural network in an end-to-end manner using the set of training images and the corresponding set of ground truth segmentation masks by configuring the processing circuitry to: down-sample a training image of the set of training images through the multi-layer contraction convolutional neural network to generate an intermediate feature map, wherein a resolution of the intermediate feature map is lower than a resolution of the training image; up-sample the intermediate feature map through the multi-layer expansion convolutional neural network to generate a first feature map and a second feature map, wherein a resolution of the second feature map is larger than the resolution of the first feature map; generate, based on the first feature map and the second feature map, a predictive segmentation mask for the training image; generate, based on a loss function, an end loss based on a difference between the predictive segmentation mask and a ground truth segmentation mask corresponding to the training image; back-propagating, by the computer, the end loss through the full convolutional neural network; and minimizing, by the computer, the end loss by adjusting a set of training parameters of the fully convolutional neural network using gradient descent.

The present disclosure also describes a non-transitory computer readable storage medium storing instructions. The instructions, when executed by a processor, cause the processor to receive a set of training images labeled with a corresponding set of ground truth segmentation masks. The instructions, when executed by a processor, cause the processor to establish a fully convolutional neural network comprising a multi-layer contraction convolutional neural network and an expansion convolutional neural network connected in tandem. The instructions, when executed by a processor, cause the processor to iteratively train the full convolution neural network in an end-to-end manner using the set of training images and the corresponding set of ground truth segmentation masks by causing the processor to: down-sample a training image of the set of training images through the multi-layer contraction convolutional neural network to generate an intermediate feature map, wherein a resolution of the intermediate feature map is lower than a resolution of the training image; up-sample the intermediate feature map through the multi-layer expansion convolutional neural network to generate a first feature map and a second feature map, wherein a resolution of the second feature map is larger than the resolution of the first feature map; generate, based on the first feature map and the second feature map, a predictive segmentation mask for the training image; generate, based on a loss function, an end loss based on a difference between the predictive segmentation mask and a ground truth segmentation mask corresponding to the training image; back-propagating, by the computer, the end loss through the full convolutional neural network; and minimizing, by the computer, the end loss by adjusting a set of training parameters of the fully convolutional neural network using gradient descent.

BRIEF DESCRIPTION OF THE DRAWINGS

FIG. 6B illustrates an exemplary implementation and data/logic flows of the enhanced fully convolutional neural network of FIG. 6A that combines the auxiliary segmentation masks by concatenation.

DETAILED DESCRIPTION

Introduction

Figure 1:
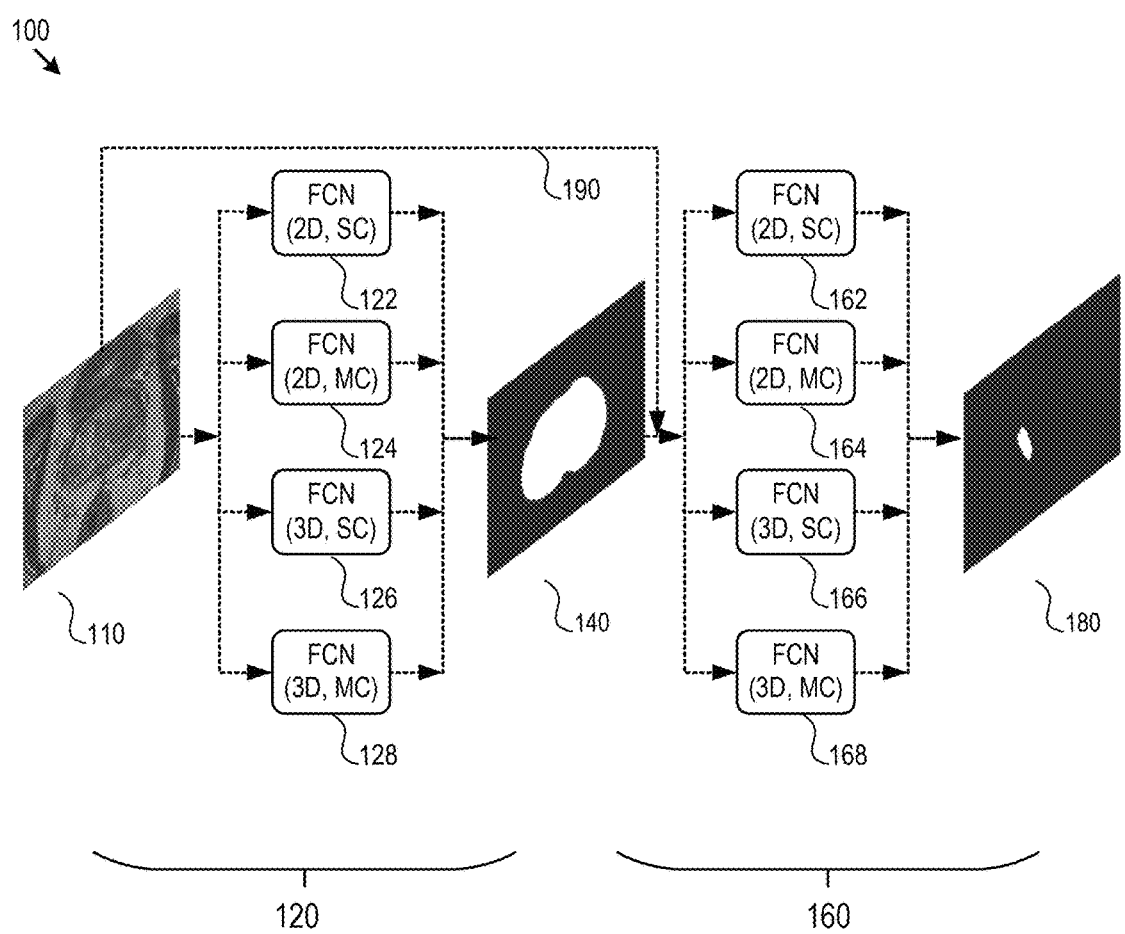
FIG. 1 illustrates a general data/logic flow of various fully convolutional neural networks (FCNs) for implementing image segmentation and object detection.

A digital image may contain one or more regions of interest (ROIs). An ROI may include a particular type of object. In many applications, only image data within the ROIs contains useful or relevant information. As such, recognition of ROIs in a digital image and identification of boundaries for these ROIs using computer vision often constitute a critical first step before further image processing is performed. A digital image may contain multiple ROIs of a same type or may contain ROIs of different types. For example, a digital image may contain only human faces or may contain both human faces of and other objects of interest. Identification of ROIs in a digital image is often alternatively referred to as image segmentation. The term "digital image" may be alternatively referred to as "image".

An image may be a two-dimensional (2D) image. A 2D image includes pixels having two-dimensional coordinates, which may be denoted along an x-axis and a y-axis. The two-dimensional coordinates of the pixels may correspond to a spatial 2D surface. The spatial 2D surface may be a planar surface or a curved surface projected from a three-dimensional object.

An image may have multiple channels. The multiple channels may be different chromatic channels, for example and not limited to, red-green-blue (RGB) color channels. The multiple channels may be different modality channels for a same object, representing images of the same object taking under different imaging conditions. For example, in conventional photography, different modalities may correspond to different combinations of focus, aperture, exposure parameters, and the like. For another example, in medical images based on Magnetic Resonance Imaging (MRI), different modality channels may include but are not limited to T2-weighted imaging (T2 W), diffusion weighted imaging (DWI), apparent diffusion coefficient (ADC) and K-trans channels.

An image may be a three-dimensional (3D) image. A 3D image includes pixels having three-dimensional coordinates, which may be denoted along an x-axis, a y-axis, and a z-axis. The three-dimensional coordinates of the pixels may correspond to a spatial 3D space. For example, MRI images in each modality channel may be three dimensional, including a plurality of slices of 2D images.

A 3D image may also have multiple channels, effectively forming a four-dimensional (4D) image. The 4D image including multiple channels may be referred to as pseudo 4D image. A 4D image includes pixels having four-dimensional coordinates, which may be denoted along an x-axis, a y-axis, a z-axis, and a channel-number.

ROIs for an image, once determined, may be represented by a digital mask containing a same number of pixels as the digital image or down-sized number of pixels from the digital image. A digital mask may be alternatively referred as a mask or a segmentation mask. Each pixel of the mask may contain a value used to denote whether a particular corresponding pixel of the digital image is among any ROI, and if it is, which type of ROI among multiple types of ROIs does it fall. For example, if there is only a single type of ROI, a binary mask is sufficient to represent all ROIs. In particular, each pixel of the ROI mask may be either zero or one, representing whether the pixel is or is not among the ROIs. For a mask capable of representing multiple types of ROI, each pixel may be at one of a number of values each corresponding to one type of ROIs. A multi-value mask, however, may be decomposed into a combination of the more fundamental binary masks each for one type of ROI.

For a 2D image, its mask may correspondingly be 2D, including pixels having two-dimensional coordinates. When an image includes multiple channels, its mask may nevertheless be a single combined mask, wherein the single mask corresponds to all the channels in the image. In some other embodiment, the mask of a multi-channel image may be a multi-channel mask, wherein each of the multiple channels of the mask corresponds to one or more channels of the multi-channel image.

For a 3D image, its mask may correspondingly be a 3D mask, including pixels having three-dimensional coordinates along an x-axis, a y-axis, and a z-axis. When a 3D image includes multiple channels, its mask may be a three-dimensional mask having either a single channel or multiple channels, similar to the 2D mask described above.

ROI masks are particularly useful for further processing of the digital image. For example, an ROI mask can be used as a filter to determine a subset of image data that are among particular types of ROIs and that need be further analyzed and processed. Image data outside of these particular types of ROIs may be removed from further analysis. Reducing the amount of data that need to be further processed may be advantageous in situations where processing speed is essential and memory space is limited. As such, automatic identification of ROIs in a digital image presents a technological problem to be overcome before further processing can be performed on the data which form the digital image.

ROI identification and ROI mask generation, or image segmentation may be implemented in various applications, including but not limited to face identification and recognition, object identification and recognition, satellite map processing, and general computer vision and image processing. For example, ROI identification and segmentation may be implemented in medical image processing. Such medical images may include but are not limited to Computed Tomography (CT) images, Magnetic Resonance Imaging (MRI) images, ultrasound images, X-Ray images, and the like. In Computer-Aided Diagnosis (CAD), a single or a group of images may first be analyzed and segmented into ROIs and non-ROIs. One or more ROI masks, alternatively referred to as segmentation masks, may be generated. An ROI in a medical image may be specified at various levels depending on the applications. For example, an ROI may be an entire organ. As such, a corresponding binary ROI mask may be used to mask the location of the organ tissues and the regions outside of the ROI and that are not part of the organ. For another example, an ROI may represent a lesion in an organ or tissue of one or more particular types in the organ. These different levels of ROIs may be hierarchical. For example, a lesion may be part of an organ.

The present disclosure may be particularly applied to different types of images by imaging various types of human tissues or organs to perform ROI identification and ROI mask generation and image segmentation, for example, including but not limited to, brain segmentation, pancreas segmentation, lung segmentation, or prostate segmentation.

In one embodiment, MR images of prostate from one or more patient may be processed using computer aided diagnosis (CAD). Prostate segmentation for marking the boundary of the organ of prostate is usually the first step in a prostate MR image processing and plays an important role in computer aided diagnosis of prostate diseases. One key to prostate segmentation is to accurately determine the boundary of the prostate tissues, either normal or pathological. Because images of normal prostate tissues may vary in texture and an abnormal prostate tissue may additionally contain patches of distinct or varying texture and patterns, identification of prostate tissues using computer vision may be particularly challenging. Misidentifying a pathological portion of the prostate tissue as not being part of the prostate and masking it out from subsequent CAD analysis may lead to unacceptable false diagnostic negatives. Accordingly, the need to accurately and reliably identify an ROI in a digital image such as a medical image of a prostate or other organs is critical to proper medical diagnosis.

Segmentation of images may be performed by a computer using a model developed using deep neural network-based machine learning algorithms. For example, a segmentation model may be based on Fully Convolutional Network (FCN) or Deep Convolutional Neural Networks (DCNN). Model parameters may be trained using labeled images. The image labels in this case may contain ground truth masks, which may be produced by human experts or via other independent processes. The FCN may contain only multiple convolution layers-. In an exemplary implementation, digital images of lungs may be processed by such neural networks for lung segmentation and computer aided diagnosis. During the training process, the model learns various features and patterns of lung tissues using the labeled images. These features and patterns include both global and local features and patterns, as represented by various convolution layers of the FCN. The knowledge obtained during the training process is embodied in the set of model parameters representing the trained FCN model. As such, a trained FCN model may process an input digital image with unknown mask and output a predicted segmentation mask. It is critical to architect the FCN to facilitate efficient and accurate learning of image features of relevance to a particular type of images.

A System to Perform CAD Using FCN

As FIG. 1 shows, a system 100 for CAD using a fully convolutional network (FCN) may include two stages: tissue segmentation and lesion detection. A first stage 120 performs tissue (or organ) segmentation from images 110 to generate tissue segmentation mask 140. A second stage 160 performs lesion detection from the tissue segmentation mask 140 and the images 110 to generate the lesion mask 180. In some implementations, the lesion mask, may be non-binary. For example, within the organ region of the image 110 as represented by the segmentation mask 140, there may be multiple lesion regions of different pathological types. The lesion mask 180 thus may correspondingly be non-binary as discussed above, and contains both special information (as to where the lesions are) and information as to the type of each lesion. According to the lesion mask 180, the system may generate a diagnosis with a certain probability for a certain disease. A lesion region may be portions of the organ containing cancer, tumor, or the like. In some embodiments, the system may only include the stage of tissue segmentation 120. In other embodiments, the system may only include the stage of lesion detection 160. In each stage of the first stage 120 or the second stage 160, an FCN of a slightly variation may be used. The first stage 120 and the second stage 160 may use the same type of FCN, or may use different type of FCN. The FCNs for stage 120 and 160 may be separately or jointly trained.

In one exemplary implementation, the tissue or organ may be a prostate, and CAD of prostate may be implemented in two steps. The first step may include determining a segmentation boundary of prostate tissue by processing input MR prostate images, producing an ROI mask for the prostate; and the second step includes detecting a diseased portion of the prostate tissue, e.g., a prostate tumor or cancer, by processing the ROI masked MR images of the prostate tissue. In another embodiment, MR images of prostate from one or more patients may be used in computer aided diagnosis (CAD). For each patient, volumetric prostate MR images is acquired with multiple channels from multi-modalities including, e.g., T2 W, DWI, ADC and K-trans, where ADC maps may be calculated from DWI, and K-trans images may be obtained using dynamic contrast enhanced (DCE) MR perfusion.

The FCN may be adapted to the form of the input images (either two-dimensional images or three-dimensional images, either multichannel or single-channel images). For example, the FCN may be adapted to include features of an appropriate number of dimensions for processing a single channel 2D or 3D images or a multichannel 2D or 3D images.

In one embodiment, for example, the images 110 may be one or more 2D images each with a single channel (SC). The first stage 120 may use two-dimensional single-channel FCN (2D, SC) 122 to perform tissue segmentation to obtain the segmentation mask 140 of an input image 110. The segmentation mask 140 may be a single 2D mask (or a mask with single channel). The second stage 160 may use two-dimensional single-channel FCN (2D, SC) 162 to perform lesion detection. The FCN (2D, SC) 162 operates on the single channel segmentation mask 140 and the single channel image 110 (via arrow 190) to generate the lesion mask 180. Accordingly, the lesion mask 180 may be a single-channel 2D mask.

In a second embodiment, the images 110 may be one or more 2D images each with multiple channels (MC). The multiple channels may be different chromatic channels (e.g., red, blue, and green colors) or other different imaging modality channels (e.g., T2 W, DWI, ADC and K-trans for MR imaging). The first stage 120 may use two-dimensional single-channel FCN (2D, SC) 122 to perform tissue segmentation of multiple channels of an input image 110 to obtain multi-channel segmentation mask 140. In particular, since the two-dimensional single-channel FCN (2D, SC) 122 is used in the tissue segmentation, each channel of the multi-channel image 110 may be regarded as independent from other channels, and thus each channel may be processed individually. Therefore, the segmentation mask 140 may be a 2D mask with multiple channels. The second stage 160 may use two dimensional multi-channel FCN (2D, MC) 164 to perform lesion detection. The FCN (2D, MC) 164 may operate simultaneously on the multi-channel segmentation mask 140 and the multi-channel image 110 to generate the lesion mask 180. The two-dimensional multi-channel FCN (2D, MC) 164 may process the multi-channel mask 140 and the multi-channel image 110 in a combined manner to generate a single-channel lesion mask 180.

In a third embodiment, the images 110 may be one or more 2D images with multiple channels. The first stage 120 may use two-dimensional multi-channel FCN (2D, MC) 124 to perform tissue segmentation of a multi-channel image 110 in a combined manner to obtain a single-channel segmentation mask 140. The second stage 160 may use two-dimensional single-channel FCN (2D, SC) 162 to perform lesion detection in the single channel mask 140. In particular, the two-dimensional single-channel FCN (2D, SC) 162 operates on the segmentation mask 140 and the multi-channel image 110 to generate a multi-channel lesion mask 180.

In a fourth embodiment, the images 110 may be one or more 2D images with multiple channels. The first stage 120 may use two-dimensional multi-channel FCN (2D, MC) 124 to perform tissue segmentation on the multi-channel image 110 to obtain a single-channel segmentation mask 140. The second stage 160 may use two-dimensional multi-channel FCN (2D, MC) 164 to perform lesion detection. The two-dimensional multi-channel FCN (2D, MC) 164 operates on the single-channel segmentation mask 140 and the multi-channel images 110 to generate a single-channel lesion mask 180.

In a fifth embodiment, the images 110 may be one or more 3D images with a single channel. The first stage 120 may use three-dimensional single-channel FCN (3D, SC) 126 to perform tissue segmentation of a single channel image 110 to obtain a three dimensional single-channel segmentation mask 140. The second stage 160 may use three-dimensional single-channel FCN (3D, SC) 166 to perform lesion detection. The FCN (3D, SC) 166 operates on the single-channel segmentation mask 140 and the single-channel image 110 to generate a three-dimensional single-channel lesion mask 180.

In a sixth embodiment, the images 110 may be one or more 3D images with multiple channels. The multiple channels may be different chromatic channels (e.g., red, blue, and green colors) or other different modality channels (e.g., T2 W, DWI, ADC and K-trans for MR imaging). The first stage 120 may use three-dimensional single-channel FCN (3D, SC) 126 to perform tissue segmentation to obtain three-dimensional multi-channel segmentation mask 140. In particular, each channel may be regarded as independent from other channels, and thus each channel is processed individually by the FCN (3D, SC) 126. The second stage 160 may use three-dimensional single-channel FCN (3D, SC) 166 to perform lesion detection. The FCN (3D, SC) 166 operates on the multi-channel segmentation mask 140 and the multi-channel images 110 to generate the lesion mask 180. Since single-channel FCN (3D, SC) 166 is used in the lesion detection, each channel of the multiple channels may be processed independent. Therefore, the lesion mask 180 may be 3D multi-channel mask.

In a seventh embodiment, the images 110 may be one or more 3D images with multiple channels. The first stage 120 may use three-dimensional single-channel FCN (3D, SC) 126 to perform tissue segmentation to obtain the segmentation mask 140. Since FCN (3D, SC) 126 is used in the tissue segmentation, each channel may be regarded as independent from other channels, and thus each channel may be processed individually. Therefore, the segmentation mask 140 may be three-dimensional multi-channel mask. The second stage 160 may use three-dimensional multi-channel FCN (3D, MC) 168 to perform lesion detection. The FCN (3D, MC) 168 operates on the multi-channel segmentation mask 140 and the multi-change image 110 to generate the lesion mask 180. Since multi-channel FCN (3D, MC) 168 is used in the lesion detection, multiple channels may be processed in a combined/aggregated manner. Therefore, the lesion mask 180 may be three-dimensional single channel mask.

In an eighth embodiment, the images 110 may be one or more 3D images with multiple channels. The first stage 120 may use three-dimensional multi-channel FCN (3D, MC) 128 to perform tissue segmentation of the 3D multi-channel image 110 in an aggregated manner to obtain a three-dimensional single-channel segmentation mask 140. The second stage 160 may use three-dimensional single-channel FCN (3D, SC) 166 to perform lesion detection. The FCN (3D, SC) 166 operates on the single-channel segmentation mask 140 and the multi-channel images 110 to generate three-dimensional multi-channel lesion mask 180.

In a ninth embodiment, the images 110 may be one or more 3D images with multiple channels. The first stage 120 may use three-dimensional multi-channel FCN (3D, MC) 128 to perform tissue segmentation of the multi-channel image 110 in an aggregated manner to obtain three-dimensional single-channel segmentation mask 140. The second stage 160 may use three-dimensional multi-channel FCN (3D, MC) 168 to perform lesion detection. The FCN (3D, MC) 168 operates on the single-channel segmentation mask 140 and the multi-channel image 110 to generate three-dimensional single-channel lesion mask 180 in an aggregated manner.

Optionally, when the total z-axis depth of a 3D image 110 is relatively shallow, a 2D mask may be sufficient to serve as the mask for the 3D image having different values along z-axis. In one exemplary implementation, for a 3D image 110 with a shallow total z-axis range, a first stage 120 may use a modified FCN (3D, SC) to perform tissue segmentation to obtain the segmentation mask 140, where the segmentation mask 140 180 may be a 2D mask.

The various two or three-dimensional and single- or multi-channel FCN models discussed above are further elaborated below.

Fully Convolutional Network (FCN)

Segmentation of images and/or target object (e.g., lesion) detection may be performed by a computer using a model developed using deep neural network-based machine learning algorithms. For example, a model may be based on Fully Convolutional Network (FCN), Deep Convolutional Neural Networks (DCNN), U-net, or V-Net. Hereinafter, the term "FCN" is used in generally refer to any CNN-based model.

Model parameters may be trained using labeled images. The image labels in this case may contain ground truth masks, which may be produced by human experts or via other independent processes. The FCN may contain multiple convolution layers. An exemplary embodiment involves processing digital images of lung tissues for computer aided diagnosis. During the training process, the model learns various features and patterns of, e.g., lung tissues or prostate tissues, using the labeled images. These features and patterns include both global and local features and patterns, as represented by various convolution layers of the FCN. The knowledge obtained during the training process are embodied in the set of model parameters representing the trained FCN model. As such, a trained FCN model may process an input digital image with unknown mask and output a predicted segmentation mask.

The present disclosure describes an FCN with different variations. The FCN is capable of performing tissue segmentation or lesion detection on 2D or 3D images with single or multiple channels. 3D images are used as an example in the embodiment below. 2D images can be processed similarly as 2D images may be regarded as 3D images with one z-slice, i.e., a single z-axis value.

Figure 2:
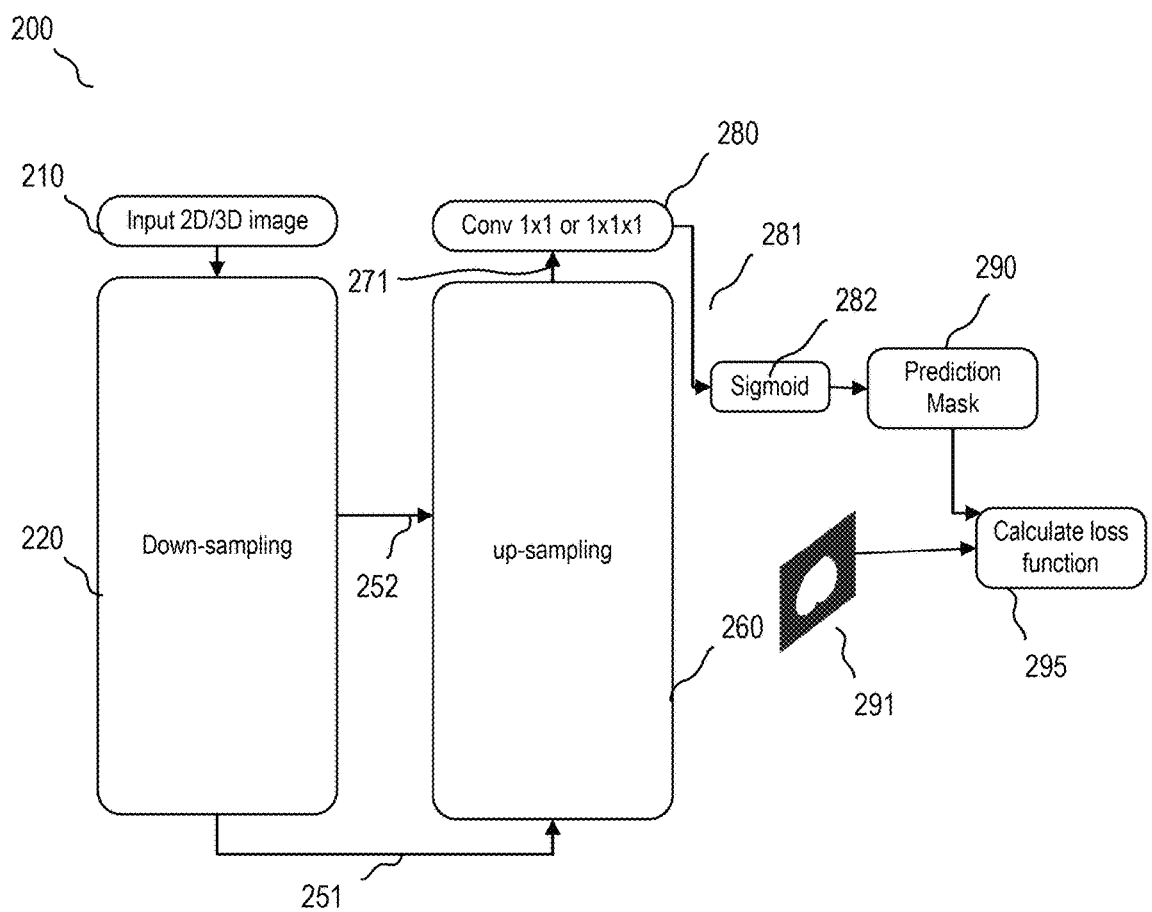
FIG. 2 illustrates an exemplary general implementation and data/logic flows of the fully convolutional neural network of FIG. 1.

An exemplary FCN model for predicting a segmentation/lesion mask for an input digital image is shown as FCN model 200 in FIG. 2. The FCN model 200 may be configured to process input 2D/3D images 210. As an example for the illustration below, the input image may be 3D and may be of an exemplary size 128×128×24, i.e., 3D images having a size of 128 along x-axis, a size of 128 along y-axis, and a size of 24 along z-axis.

A down-sampling path 220 may comprise a contraction neural network which gradually reduces the resolution of the 2D/3D images to generate feature maps with smaller resolution and larger depth. For example, the output 251 from the down-sampling part 220 may be feature maps of 16×16×3 with depth of 128, i.e., the feature maps having a size of 16 along x-axis, a size of 16 along y-axis, a size of 3 along z-axis, and a depth of 128 (exemplary only, and corresponding to number of features).

The down-sampling path 220 is contracting because it processes an input image into feature maps that progressively reduce their resolutions through one or more layers of the down-sampling part 220. As such, the term "contraction path" may be alternatively referred to as "down-sampling path".

The FCN model 200 may include an up-sampling path 260, which may be an expansion path to generate high-resolution feature maps for voxel-level prediction. The output 251 from the down-sampling path 220 may serve as an input to the up-sampling path 260. An output 271 from the up-sampling path 260 may be feature maps of 128×128×24 with depth of 16, i.e., the feature maps having a size of 128 along x-axis, a size of 128 along y-axis, a size of 24 along z-axis, and a depth of 16.

The up sampling path 260 processes these feature maps in one or more layers and in an opposite direction to that of the down-sampling path 220 and eventually generates a segmentation mask 290 with a resolution similar or equal to the input image. As such, the term "expansion path" may be alternatively referred to as "up-sampling path".

The FCN model 200 may include a convolution step 280, which is performed on the output of the up-sampling stage with highest resolution to generate map 281. The convolution operation kernel in step 280 may be 1×1×1 for 3D images or 1×1 for 2D images.

The FCN model 200 may include a rectifier, e.g., sigmoid step 280, which take map 281 as input to generate voxel-wise binary classification probability prediction mask 290.

Depending on specific applications, the down-sampling path 220 and up-sampling path 260 may include any number of convolution layers, pooling layers, or de-convolutional layers. For example, for a training set having a relatively small size, there may be 6-50 convolution layers, 2-6 pooling layers and 2-6 de-convolutional layers. Specifically as an example, there may be 15 convolution layers, 3 pooling layers and 3 de-convolutional layers. The size and number of features in each convolutional or de-convolutional layer may be predetermined and are not limited in this disclosure.

The FCN model 200 may optionally include one or more steps 252 connecting the feature maps within the down-sampling path 220 with the feature maps within the up-sampling path 260. During steps 252, the output of de-convolution layers may be fed to the corresponding feature maps generated in the down-sampling path 220 with matching resolution (e.g., by concatenation, as shown below in connection with FIG. 4). Steps 252 may provide complementary high-resolution information into the up-sampling path 260 to enhance the final prediction mask, since the de-convolution layers only take coarse features from low-resolution layer as input. Feature maps at different convolution layer and with different level of resolution from the contraction CNN may be input into the expansion CNN as shown by the arrow 252.

The model parameters for the FCN include features or kernels used in various convolutional layers for generating the feature maps, their weight and bias, and other parameters. By training the FCN model using images labeled with ground truth segmentation masks, a set of features and other parameters may be learned such that patterns and textures in an input image with unknown label may be identified. In many circumstances, such as medical image segmentation, this learning process may be challenging due to lack of a large number of samples of certain important texture or patterns in training images relative to other texture or patterns. For example, in a lung image, disease image patches are usually much fewer than other normal image patches and yet it is extremely critical that these disease image patches are correctly identified by the FCN model and segmented as part of the lung. The large number of parameters in a typical multilayer FCN tend to over-fit the network even after data augmentation. As such, the model parameters and the training process are preferably designed to reduce overfitting and promote identification of features that are critical but scarce in the labeled training images.

Once the FCN 200 described above is trained, an input image may then be processed through the down-sampling/contraction path 220 and up-sampling/expansion path 260 to generate a predicted segmentation mask. The predicted segmentation mask may be used as a filter for subsequent processing of the input image.

The training process for the FCN 200 may involve forward-propagating each of a set of training images through the down-sampling/contraction path 220 and up-sampling/expansion path 260. The set of training images are each associated with a label, e.g., a ground truth mask 291. The training parameters, such as all the convolutional features or kernels, various weights, and bias may be, e.g., randomly initialized. The output segmentation mask as a result of the forward-propagation may be compared with the ground truth mask 291 of the input image. A loss function 295 may be determined. In one implementation, the loss function 295 may include a soft max cross-entropy loss. In another implementation, the loss function 295 may include dice coefficient (DC) loss function. Other types of loss function are also contemplated. Then a back-propagation through the expansion path 260 and then the contraction path 220 may be performed based on, e.g., stochastic gradient descent, and aimed at minimizing the loss function 295. By iterating the forward-propagation and back-propagation for the same input images, and for the entire training image set, the training parameters may converge to provide acceptable errors between the predicted masks and ground truth masks for all or most of the input images. The converged training parameters, including but not limited to the convolutional features/kernels and various weights and bias, may form a final predictive model that may be further verified using test images and used to predict segmentation masks for images that the network has never seen before. The model is preferably trained to promote errors on the over-inclusive side to reduce or prevent false negatives in later stage of CAD based on a predicted mask.

Figure 3:
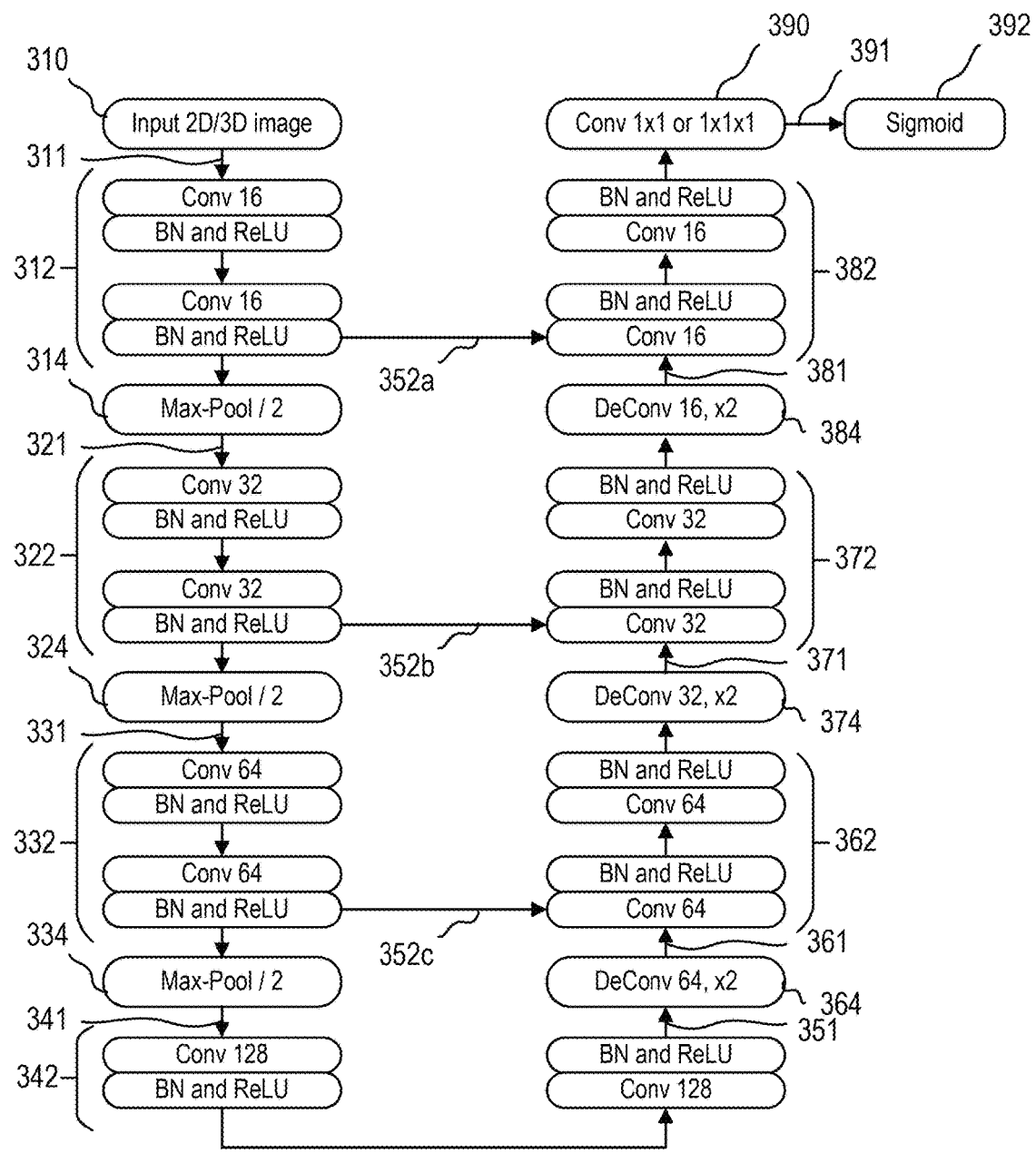
FIG. 3 illustrates an exemplary implementation and data/logic flows of the fully convolutional neural network of FIG. 1.

FIG. 3 describes one specific example of FCN. The working of the exemplary implementation of FIG. 3 is described below. More detailed description is included in U.S. application Ser. No. 15/943,392, filed on Apr. 2, 2018 by the same Applicant as the present application, which is incorporated herein by reference in its entirety.

As shown in step 310 of FIG. 3, 2D/3D images may be fed into the FCN. The 2D/3D images may be MR image patches with size 128×128×24.

The 2D/3D images 311 may be fed into step 312, which includes one or more convolutional layers, for example and not limited to, two convolutional layers. In each convolutional layer, a kernel size may be adopted and number of filters may increase or be the same. For example, a kernel size of 3×3×3 voxels may be used in the convolution sub-step in step 312. Each convolutional sub-step is followed by batch normalization (BN) and rectified-linear unit (ReLU) sub-step.

Number of features at each convolution layer may be predetermined. For example, in the particular implementation of FIG. 3, the number of features for step 312 may be 16. The output of convolution between the input and features may be processed by a ReLU to generate stacks of feature maps. The ReLUs may be of any mathematical form. For example, the ReLUs may include but are not limited to noisy ReLUs, leaky ReLUs, and exponential linear units.

After each convolution of an input with a feature in each layer, the number of pixels in a resulting feature map may be reduced. For example, a 100-pixel by 100-pixel input, after convolution with a 5-pixel by 5-pixel feature sliding through the input with a stride of 1, the resulting feature map may be of 96 pixel by 96 pixel. Further, the input image or a feature map may be, for example, zero padded around the edges to 104-pixel by 104-pixel such that the output feature map is the 100-pixel by 100-pixel resolution. The example below may use zero padding method, so that the resolution does not change before and after convolution function.

The feature maps from step 312 may be max-pooled spatially to generate the input to a next layer below. The max-pooling may be performed using any suitable basis, e.g., 2×2, resulting in down-sampling of an input by a factor of 2 in each of the two spatial dimensions. In some implementations, spatial pooling other than max-pooling may be used. Further, different layers of 314, 324, and 334 may be pooled using a same basis or different basis, and using a same or different pooling method.

For example, after max-pooling by a factor of 2, the feature maps 321 have a size of 64×64×12. Since the number of features used in step 312 is 16. The depth of the feature maps 321 may be 16.

The feature map 321 may be fed into next convolution layer 322 with another kernel and number of features. For example, the number of features in step 322 may be number 32.

In the example shown in FIG. 3, the output from step 324 may be feature maps 331 having a size of 32×32×6. Since the number of features used in step 322 is 32. The depth of the feature maps 331 may be 32.

The feature map 331 may be fed into next convolution layer 332 with another kernel and number of features. For example, the number of features in step 332 may be number 64.

In the example shown in FIG. 3, the output from step 334 may be feature maps 341 having a size of 16×16×3. Since the number of features used in step 332 is 64. The depth of the feature maps 341 may be 64.

The feature map 341 may be fed into next convolution layer 342 with another kernel and number of features. For example, the number of features in step 342 may be number 128.

In the example shown in FIG. 3, the output from step 342 may be feature maps 351 having a size of 16×16×3. There is no size reduction between feature maps 341 and feature maps 351 because there is no max-pooling steps in between. Since the number of features used in step 342 is 128. The depth of the feature maps 351 may be 128.

The feature maps 351 of the final layer 342 of the down-sampling path may be input into an up-sampling path and processed upward through the expansion path. The expansion path, for example, may include one or more de-convolution layers, corresponding to convolution layers on the contraction path, respectively. The up-sampling path, for example, may involve increasing the number of pixels for feature maps in each spatial dimension, by a factor of, e.g., 2, but reducing the number of feature maps, i.e., reducing the depth of the feature maps. This reduction may be by a factor, e.g., 2, or this reduction may not be by an integer factor, for example, the previous layer has a depth of 128, and the reduced depth is 64.

The feature maps 351 may be fed into a de-convolution operation 364 with 2×2×2 trainable kernels to increase/expand the size of input feature maps by a factor of 2, the output of the de-convolution operation 364 may be feature maps 361 having a size of 32×32×6. Since the number of features used in the de-convolution operation 364 is 64, the depth of the feature maps 361 is 64.

The feature maps 361 may be fed into a step 362. The step 362 may include one or more convolution layers. In the example shown in FIG. 3, the step 362 includes two convolution layers. Each of the convolution layer includes a convolution function sub-step followed by batch normalization (BN) and rectified-linear unit (ReLU) sub-step.

Optionally, as connections 352a, 352b, and 352c in FIG. 3 show, at each expansion layer of 362, 372, and 382, the feature maps from the down-sampling path may be concatenated with the feature maps in the up-sampling path, respectively. Taking 352c as an example, the feature maps in step 332 of the down-sampling path has a size of 32×32×6 and a depth of 64. The feature maps 361 of the up-sampling path has a size of 32×32×6 and a depth of 64. These two feature maps may be concatenated together to form new feature maps having a size of 32×32×6 and a depth of 128. The new feature maps may be fed as the input into the step 362. The connection 352c may provide complementary high-resolution information, since the de-convolution layers only take course features from low-resolution layers as input.

The output feature maps of step 362 may be fed into de-convolution layer 374. The de-convolution layer may have a trainable kernel 2×2×2 to increase/expand the size of the input feature maps by a factor of 2. The output of the de-convolution operation 374 may be feature maps 371 having a size of 64×64×12. Since the number of features used in the de-convolution operation 374 is 32, the depth of the feature maps 371 is 32.

Optionally, as the connection 352b in FIG. 3 shows, the feature maps from step 322 in the down-sampling path may be concatenated with the feature maps 371. The feature maps in step 322 of the down-sampling path has a size of 64×64×12 and a depth of 32. The feature maps 371 of the up-sampling path has a size of 64×64×12 and a depth of 32. These two feature maps may be concatenated together to form new feature maps having a size of 64×64×12 and a depth of 64. The new feature maps may be fed as the input into the step 372.

The output feature maps of step 372 may be fed into de-convolution layer 384. The de-convolution layer may have a trainable kernel 2×2×2 to increase/expand the size of the input feature maps by a factor of 2. The output of the de-convolution operation 384 may be feature maps 381 having a size of 128×128×24. Since the number of features used in the de-convolution operation 384 is 16, the depth of the feature maps 381 is 16.

Optionally, as the connection 352a in FIG. 3 shows, the feature maps from step 312 in the down-sampling path may be concatenated with the feature maps 381. The feature maps in step 312 of the down-sampling path has a size of 128×128×24 and a depth of 16. The feature maps 371 of the up-sampling path has a size of 128×128×24 and a depth of 16. These two feature maps may be concatenated together to form new feature maps having a size of 128×128×24 and a depth of 32. The new feature maps may be fed as the input into the step 382.

The output figure maps from step 382 may be fed into a convolution step 390, which perform on the feature maps with highest resolution to generate feature maps 391. The feature maps 391 may have a size of 128×128×24 and a depth of one. The convolution operation kernel in step 390 may be 1×1×1 for 3D images or 1×1 for 2D images.

The feature maps 391 may be fed into a sigmoid step 392, which take feature maps 391 as input to generate voxel-wise binary classification probabilities, which may be further determined to be the predicted segmentation mask for the tissue or lesion.

Figure 4:
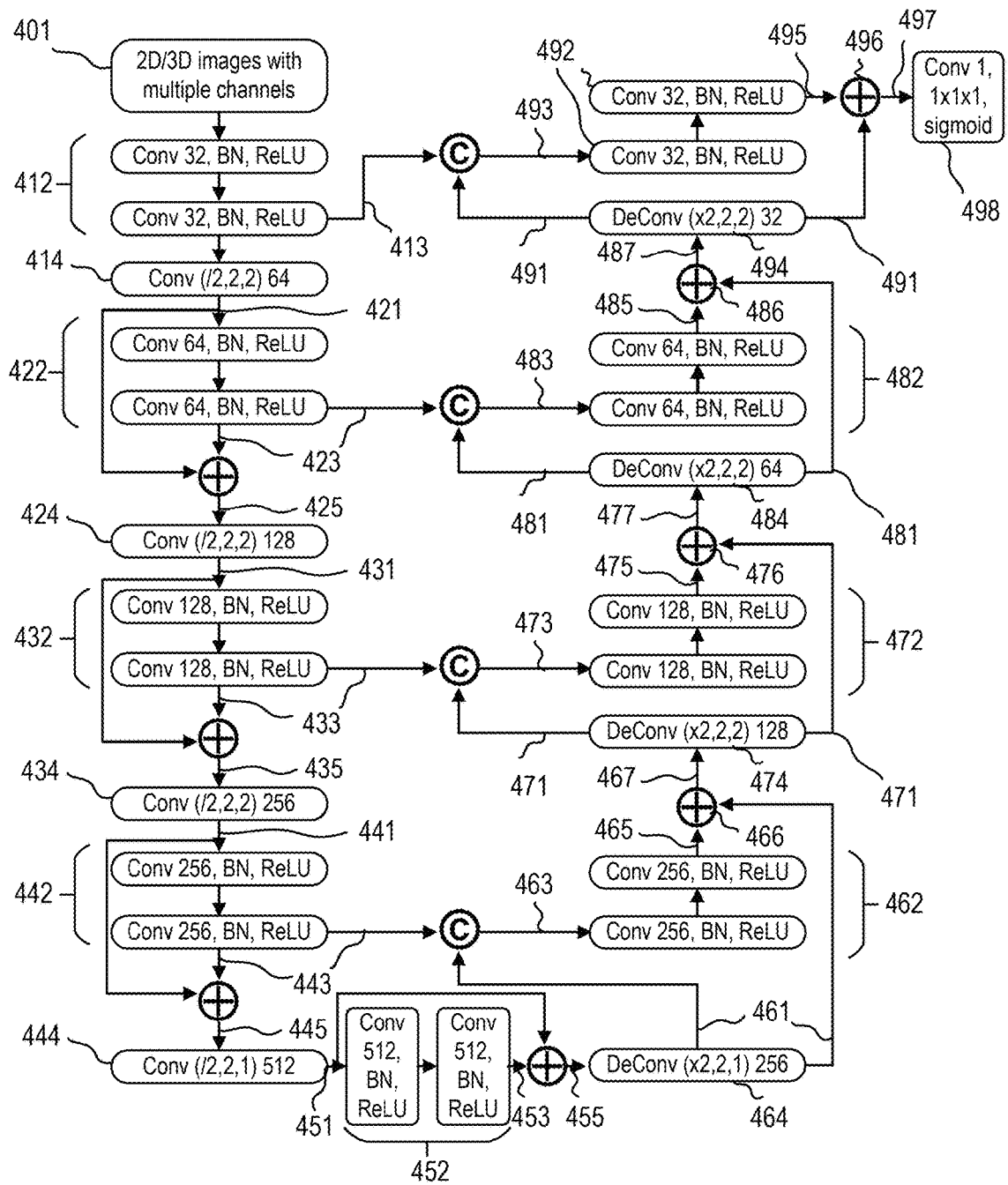
FIG. 4 illustrates another exemplary implementation and data/logic flows of the fully convolutional neural network of FIG. 1.

FIG. 4 describes another embodiment of FCN for segmentation of 2D/3D images with either single or multiple channels. In the example described below, 3D images with multiple channels may be taken as an example. However, the FCN model in this disclosure is not limited to 3D images with multiple channels (FCN (3D, MC)). For example, the FCN model in this embodiment may be applied to 2D images with multiple channels (FCN(2D, MC)), 3D images with single channel (FCN(3D, SC)), or 2D images with single channel (FCN(2D, SC)), as shown in FIG. 1.

In FIG. 4, the input 2D/3D images with multiple channels 401 may include 3D images having a size of 128×128×24 with three channels. The three channels may be multi-parametric modalities in MR imaging including T2 W, T1 and DWI with highest b-value. Or in some other situations, the three channels may include red, green, and blue chromatic channels. In one embodiment, each of the three channels may be processed independently. In another embodiment, the three channels may be processed collectively, and as such, the first convolutional layer operating on the input images 401 has a 3×3×3×3 convolutional kernels.

The FCN model in FIG. 4 may include a down-sampling/contracting path and a corresponding up-sampling/expansion path. The down-sampling/contracting path may include one or more convolutional layers 412.

The convolutional layer 412 may comprise 3×3×3 convolution kernels, batch normalization (BN), and ReLU activation function to extract high-level features. The number of features in the convolution layer 412 may be 32, so that the feature maps of the convolution layer 412 may have a size of 128×128×24 and a depth of 32.

The FCN model in FIG. 4 may include convolution layers 414 with strides greater than 1 for gradually reducing the resolution of feature maps and increase the receptive field to incorporate more spatial information. For example, the convolution layer 414 may have a stride of 2 along x-axis, y-axis, and z-axis, so that the resolution along x-axis, y-axis, and z-axis all reduced by a factor of 2. The number of features in the convolution layer 414 may be 64, so that the output feature maps 421 of the convolution layer 414 may have a size of 64×64×12 and a depth of 64.

The feature map may be fed into one or more convolution layers 422. Each of the convolutional layers 422 may comprise a 3×3×3 convolution kernels, batch normalization (BN), and ReLU activation function to extract high-level features. The number of features in the convolution layer 422 may be 64, so that the output feature maps 423 of the convolution layer 422 may have a size of 64×64×12 and a depth of 64.

At each resolution level, input feature maps may be directly added to output feature maps, which enables the stacked convolutional layers to learn a residual function. As described by operator ⊕ in FIG. 4, the feature maps 421 and 423 may be added together. The output feature maps 425 of operator ⊕ may be a summation of feature maps 421 and 423 element by element. The feature maps 425 may have a size of 64×64×12 and a depth of 64.

The feature maps 425 may be fed into a convolution layer 424 with a stride of 2 along x-axis, y-axis, and z-axis, so that the resolution along x-axis, y-axis, and z-axis is reduced by a factor of 2. The number of features in the convolution layer 424 may be 128, so that the output feature maps 431 of the convolution layer 424 may have a size of 32×32×6 and a depth of 128.

The feature map 431 may be fed into one or more convolution layers 432. Each of the convolutional layers 432 may comprise a 3×3×3 convolution kernels, batch normalization (BN), and ReLU activation function to extract high-level features. The number of features in the convolution layer 432 may be 128, so that the output feature maps 433 of the convolution layers 432 may have a size of 32×32×6 and a depth of 128.

At each resolution level, input feature maps may be directly added to output feature maps, which enables the stacked convolutional layers to learn a residual function. As described by the operator ⊕ in FIG. 4, the feature maps 431 and 433 may be added together. The output feature maps 435 of operator ⊕ may be an element by element summation of feature maps 431 and 433. The feature maps 435 may have a size of 32×32×6 and a depth of 128.

The feature maps 435 may be fed into a convolution layer 434 with a stride of 2 along x-axis, y-axis, and z-axis, so that the resolution along x-axis, y-axis, and z-axis is reduced by a factor of 2. The number of features in the convolution layer 434 may be 256, so that the output feature maps 441 of the convolution layer 434 may have a size of 16×16×3 and a depth of 256.

The feature map 441 may be fed into one or more convolution layers 442. Each of the convolutional layers 442 may comprise a 3×3×3 convolution kernels, batch normalization (BN), and ReLU activation function to extract high-level features. The number of features in the convolution layer 442 may be 256, so that the output feature maps 443 of the convolution layers 442 may have a size of 16×16×3 and a depth of 256.

Again, at each resolution level, input feature maps may be directly added to output feature maps, which enables the stacked convolutional layers to learn a residual function. As described by operator ⊕ in FIG. 4, the feature maps 441 and 443 may be added together. The output feature maps 445 of the operator ⊕ may be an element-by-element summation of feature maps 441 and 443. The feature maps 445 may have a size of 16×16×3 and a depth of 256.

Optionally, the feature maps 445 may be fed into a convolution layer 444 with a stride of 2 along x-axis and y-axis, and with a stride of 1 along z-axis, so that the resolution along x-axis and y-axis is reduced by a factor of 2 and the resolution along z-axis remains the same. The number of features in the convolution layer 444 may be 512, so that the output feature maps 451 of the convolution layer 444 may have a size of 8×8×3 and a depth of 512.

The feature map 451 may be fed into one or more convolution layers 452. Each of the convolutional layers 452 may comprise a 3×3×3 convolution kernels, batch normalization (BN), and ReLU activation function to extract high-level features. The number of features in the convolution layer 452 may be 512, so that the output feature maps 453 of the convolution layers 452 may have a size of 8×8×3 and a depth of 512.

At each resolution level, input feature maps may be directly added to output feature maps, which enables the stacked convolutional layers to learn a residual function. As described by operator ⊕ in FIG. 4, the feature maps 451 and 453 may be added together. The output feature maps 455 of operator ⊕ may be an element-by-element summation of feature maps 451 and 453. The feature maps 455 may have a size of 8×8×3 and a depth of 512.

The FCN model in FIG. 4 may include a corresponding up-sampling/expansion path to increase the resolution of feature maps generated from the down-sampling/contracting path. Optionally, in the up-sampling/expansion path, the feature maps generated in the contracting path may be concatenated with the output of de-convolutional layers to incorporate high-resolution information.

The up-sampling/expansion path may include a de-convolution layer 464. The de-convolution layer 464 may de-convolute input feature maps 455 to increase its resolution by a factor of 2 along x-axis and y-axis. The output feature maps 461 of the de-convolution layer 464 may have a size of 16×16×3. The number of features in the de-convolution layer 464 may be 256, so that the output feature maps 461 of the convolution layer 464 may have a depth of 256.

As denoted by operator "ⓒ" in FIG. 4, the feature maps 443 generated from the convolution layer 442 may be concatenated with the feature maps 461 generated from the de-convolution layer 464. The feature maps 443 may have a size of 16×16×3 and a depth of 256. The feature maps 461 may have a size of 16×16×3 and a depth of 256. The cascaded feature maps 463 may correspondingly have a size of 16×16×3 and a depth of 512.

The feature map 463 may be fed into one or more convolution layers 462. Each of the convolutional layers 462 may comprise a 3×3×3 convolution kernels, batch normalization (BN), and ReLU activation function to extract high-level features. The number of features in the convolution layer 462 may be 256, so that the output feature maps 465 of the convolution layers 462 may have a size of 16×16×3 and a depth of 256.

As described by the operator ⊕ 466 in FIG. 4, the feature maps 461 and 465 may be added together. The output feature maps 467 of the operator ⊕ 466 may be an element-by-element summation of feature maps 461 and 465. The feature maps 467 may have a size of 16×16×3 and a depth of 512.

The feature maps 467 may be fed into a de-convolution layer 474. The de-convolution layer 474 may de-convolute input feature maps 467 to increase its resolution by a factor of 2 along x-axis, y-axis and z-axis. The output feature maps 471 of the de-convolution layer 474 may have a size of 32×32×6. The number of features in the de-convolution layer 474 may be 128, so that the output feature maps 471 of the convolution layer 474 may have a depth of 128.

As denoted by operator "ⓒ" in FIG. 4, the feature maps 433 generated from the convolution layer 432 may be concatenated with the feature maps 471 generated from the de-convolution layer 474. The feature maps 433 may have a size of 32×32×6 and a depth of 128. The feature maps 471 may have a size of 32×32×6 and a depth of 128. The concatenated feature maps 473 may correspondingly have a size of 32×32×6 and a depth of 256.

The feature map 473 may be fed into one or more convolution layers 472. Each of the convolutional layers 472 may comprise a 3×3×3 convolution kernels, batch normalization (BN), and ReLU activation function to extract high-level features. The number of features in the convolution layer 472 may be 128, so that the output feature maps 475 of the convolution layers 472 may have a size of 32×32×6 and a depth of 128.

As described by operator ⊕ 476 in FIG. 4, the feature maps 471 and 475 may be added together. The output feature maps 477 of the operator ⊕ 476 may be an element-by-element summation of feature maps 471 and 475. The feature maps 477 may have a size of 32×32×6 and a depth of 128.

The feature maps 477 may be fed into a de-convolution layer 484. The de-convolution layer 484 may de-convolute input feature maps 477 to increase its resolution by a factor of 2 along x-axis, y-axis and z-axis. The output feature maps 481 of the de-convolution layer 484 may have a size of 64×64×12. The number of features in the de-convolution layer 484 may be 64, so that the output feature maps 481 of the convolution layer 484 may have a depth of 64.

As denoted by operator "©" in FIG. 4, the feature maps 423 generated from the convolution layer 422 may be concatenated with the feature maps 481 generated from the de-convolution layer 484. The feature maps 423 may have a size of 64×64×12 and a depth of 64. The concatenated feature maps 481 may have a size of 64×64×12 and a depth of 64. The feature maps 483 may correspondingly have a size of 64×64×12 and a depth of 128.

The feature map 483 may be fed into one or more convolution layers 482. Each of the convolution layers 482 may comprise a 3×3×3 convolution kernels, batch normalization (BN), and ReLU activation function to extract high-level features. The number of features in the convolution layer 482 may be 64, so that the output feature maps 485 of the convolution layers 482 may have a size of 64×64×12 and a depth of 64.

As described by operator ⊕ 486 in FIG. 4, the feature maps 481 and 485 may be added together. The output feature maps 487 of ⊕ 486 may be an element-by-element summation of feature maps 481 and 485. The feature maps 487 may have a size of 64×64×12 and a depth of 64.

The feature maps 487 may be fed into a de-convolution layer 494. The de-convolution layer 494 may de-convolute input feature maps 487 to increase its resolution by a factor of 2 along x-axis, y-axis and z-axis. The output feature maps 491 of the de-convolution layer 494 may have a size of 128×128×24. The number of features in the de-convolution layer 494 may be 32, so that the output feature maps 491 of the convolution layer 494 may have a depth of 32.

As denoted by operator "©" in FIG. 4, the feature maps 413 generated from the convolution layer 412 may be concatenated with the feature maps 491 generated from the de-convolution layer 494. The feature maps 413 may have a size of 128×128×24 and a depth of 32. The feature maps 491 may have a size of 128×128×24 and a depth of 32. The concatenated feature maps 493 may correspondingly have a size of 128×128×24 and a depth of 64.

The feature map 493 may be fed into one or more convolution layers 492. Each of the convolution layers 492 may comprise a 3×3×3 convolution kernels, batch normalization (BN), and ReLU activation function to extract high-level features. The number of features in the convolution layer 492 may be 32, so that the output feature maps 495 of the convolution layers 492 may have a size of 128×128×24 and a depth of 32.

As described by operator ⊕ 496 in FIG. 4, the feature maps 491 and 495 may be added together. The output feature maps 497 of ⊕ 496 may be an element-by-element summation of feature maps 491 and 495. The feature maps 497 may have a size of 128×128×24 and a depth of 32.

The feature maps 497 may be fed into a convolutional layer 498 to generate voxel-wise binary classification probabilities. The convolutional layer 498 may include a 1×1×1 kernel and sigmoid activation function.

During training phase, Dice loss may be adopted as the objective function, and the dice loss may be expressed as $$\text{Dice loss} = \frac{2\sum_{i}^{N} g_i p_i}{\sum_{i}^{N} g_i + \sum_{i}^{N} p_i}$$

Where $g_i$ and $p_i$ are the ground truth label and predicted label respectively. Post-processing steps may be then applied to refine the initial segmentation generated by the FCN model. In some embodiments, specifically, a 3D Gaussian filter may be used to smooth the predicted probability maps and a connected component analysis may be used to remove small isolated components.

Fully Convolutional Network (FCN) Enhanced by a Coarse-to-Fine Architecture

The present disclosure describes an FCN with coarse-to-fine architecture, which takes advantages of residual learning and deep supervision, in order to improve the segmentation performance and training efficiency.

Figure 5:
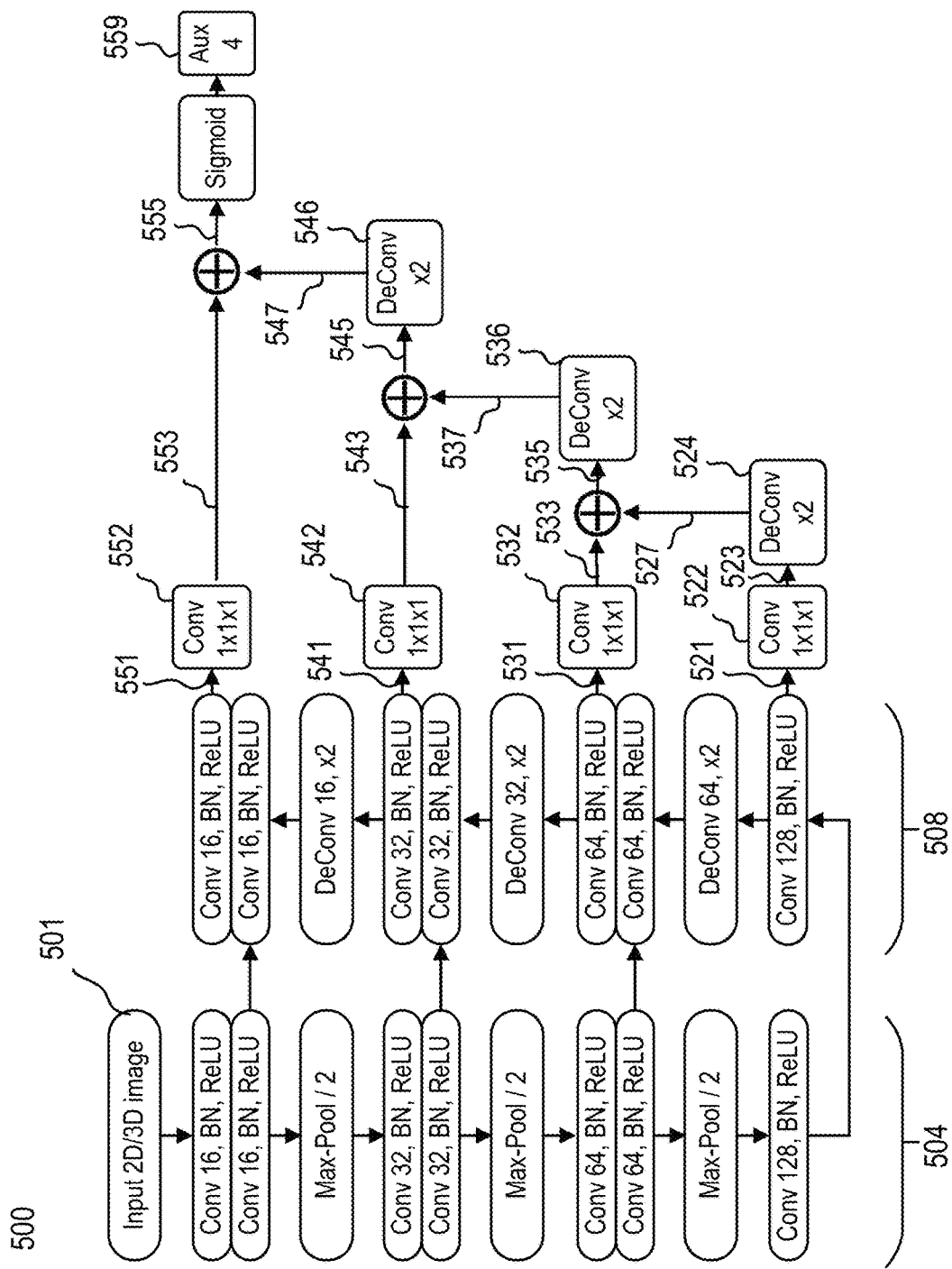
FIG. 5 illustrates an exemplary implementation and data/logic flows of the fully convolutional neural network enhanced by a coarse-to-fine architecture.

One embodiment of such an FCN model is shown as 500 in FIG. 5. The FCN model includes a down-sampling/contraction path 504 and an up-sampling/expansion path 508, similar to the model described in FIG. 3. Auxiliary convolutional layers 522, 532, 542, and 552 may be connected to feature maps 521, 531, 541, and 551 with progressive resolution in the expansion path 508, in order to generate single feature maps which are then up-sampled and fed into a sigmoid function to obtain auxiliary predictions 559.

The auxiliary predictions 559 may be used to further determine the mask for the organ or lesion. During the training process using input images for the FCN model in FIG. 5, the output segmentation mask generated from the auxiliary predictions 559 may be compared with the ground truth mask of the input images. A loss function may be determined. In one implementation, the loss function may include a soft max cross-entropy loss. In another implementation, the loss function may include dice coefficient (DC) loss function.

The input 2D/3D images 501 in FIG. 5 may be, for example and not limited to, 3D images having a size of 128×128×24. In the expansion path 508, the feature maps 521 may have a size of 16×16×3 and a depth of 128; the feature maps 531 may have a size of 32×32×6 and a depth of 64; the feature maps 541 may have a size of 64×64×12 and a depth of 32; and the feature maps 551 may have a size of 128×128×24 and a depth of 16.

The feature maps 521 may be fed into an auxiliary convolutional layer 522. The auxiliary convolutional layer 522 may have a kernel size of 1×1×1 for 3D images or 1×1 for 2D images. The output feature maps 523 may have a size of 16×16×3 and a depth of one. The output feature maps 523 may be fed into a de-convolutional layer 524 to increase the resolution, so as to generate feature maps 527 having a size of 32×32×6.

The feature maps 531 may be fed into an auxiliary convolutional layer 532. The auxiliary convolutional layer 532 may have a kernel size of 1×1×1 for 3D images or 1×1 for 2D images. The output feature maps 533 may have a size of 32×32×6 and a depth of one. The output feature maps 533 may be added onto the feature maps 527 in an element-by-element manner to generate feature maps 535. The feature maps 535 may have a size of 32×32×6 and a depth of one. The feature maps 535 may be fed into a de-convolutional layer 536 to increase the resolution, so as to generate feature maps 537 having a size of 64×64×12.

The feature maps 541 may be fed into an auxiliary convolutional layer 542. The auxiliary convolutional layer 542 may have a kernel size of 1×1×1 for 3D images or 1×1 for 2D images. The output feature maps 543 may have a size of 64×64×12 and a depth of one. The output feature maps 543 may be added onto the feature maps 537 element-by-element to generate feature maps 545. The feature maps 545 may have a size of 64×64×12 and a depth of one. The feature maps 545 may be fed into a de-convolutional layer 546 to increase the resolution, so as to generate feature maps 547 having a size of 128×128×24.

The feature maps 551 may be fed into an auxiliary convolutional layer 552. The auxiliary convolutional layer 552 may have a kernel size of 1×1×1 for 3D images or 1×1 for 2D images. The output feature maps 553 may have a size of 128×128×24 and a depth of one. The output feature maps 553 may be added onto the feature maps 547 in element-by-element to generate feature maps 555. The feature maps 555 may have a size of 128×128×64 and a depth of one.

The feature maps 555 may be fed into a sigmoid function, which take feature maps 555 as input to generate auxiliary 4 (559), which includes voxel-wise binary classification probabilities and may be further processed to be the mask for the tissue or lesion.

Figure 6A:
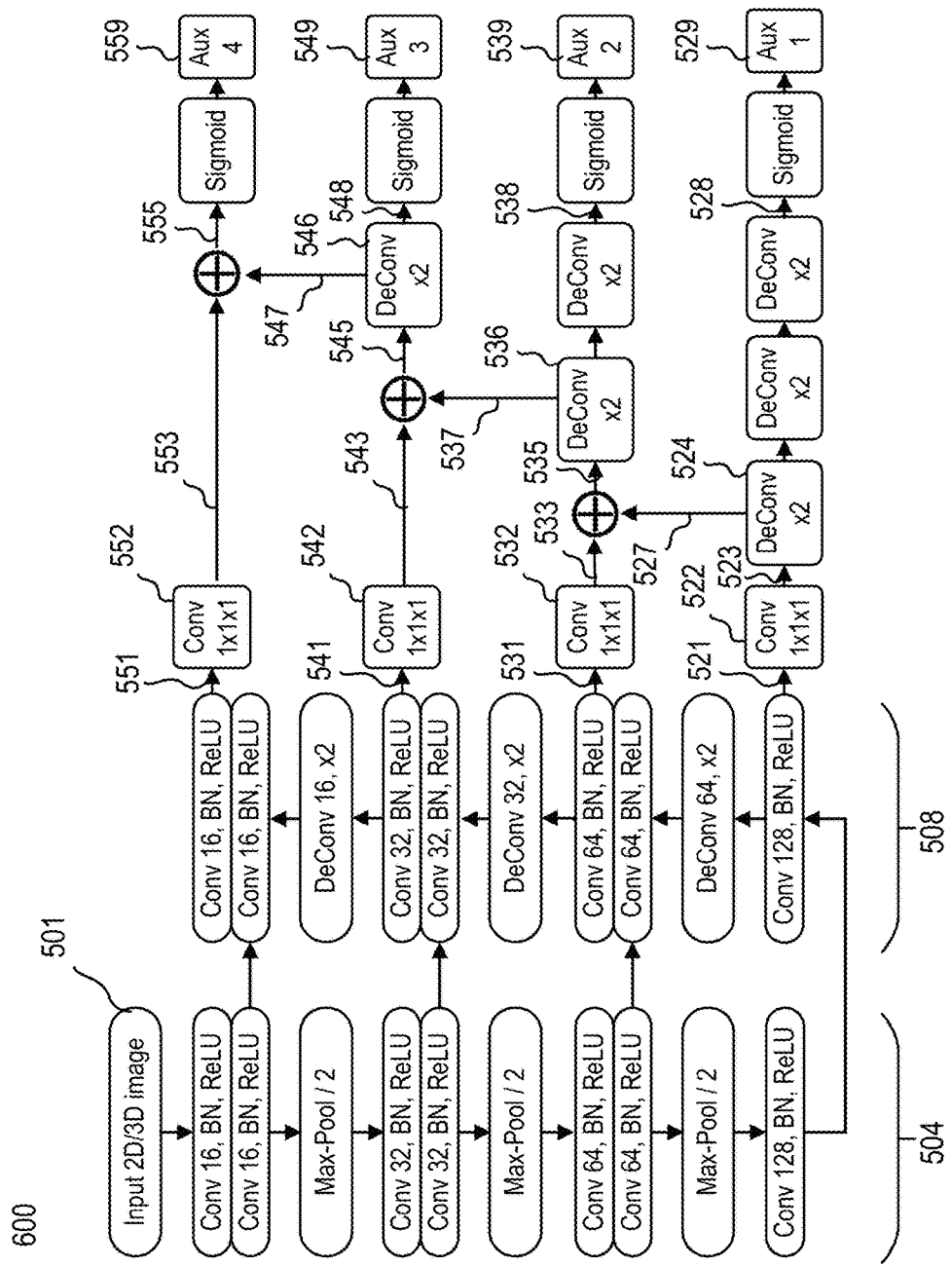
FIG. 6A illustrates an exemplary implementation and data/logic flows of the fully convolutional neural network having a coarse-to-fine architecture with auxiliary segmentation masks.

Another enhanced embodiment of an FCN model 600 is shown in FIG. 6A. In the FCN model 600, the feature maps with reduced resolutions in the up-sampling/expansion path may be fed into auxiliary convolutional layers, up-sampled to an original resolution, and then fed into a sigmoid function to generate their corresponding auxiliary predictions. The one or more auxiliary predictions may be combined together to generate the mask for the tissue or lesion.

In particular, the feature maps 521 may be fed into an auxiliary convolutional layer 522 to generate feature maps 523 having a size of 16×16×3 and a depth of one. The output feature maps 523 may be fed into one or more de-convolutional layers to generate feature maps 528 and expand the resolution from 16×16×3 to 128×128×24. In the embodiment as shown in FIG. 6A, the one or more de-convolutional layers with respect to feature map 521 (lowest resolution layer in the expansion network) may include three de-convolutional layers and each of the three de-convolutional layers may expand the resolution by a factor of 2 in x-axis, y-axis and z-axis. In another embodiment, the one or more de-convolutional layers with respect to feature map 521 (lowest resolution layer in the expansion network) may include one de-convolutional layer, which may expand the resolution by a factor of 8 in x-axis, y-axis and z-axis. As such, the feature maps 528 may recover the full resolution and may be then fed into a sigmoid function to obtain auxiliary 1 (529).

The feature maps 535 at the second lowest resolution layer may be fed into one or more de-convolutional layers to generate feature maps 538 and expand the resolution from 32×32×6 to 128×128×24 (full resolution). In the embodiment as shown in FIG. 6A, the one or more de-convolutional layers here may include two de-convolutional layers and each of the two de-convolutional layers may expand the resolution by a factor of 2 in x-axis, y-axis and z-axis. In another embodiment, the one or more de-convolutional layers may include one de-convolutional layer, which may expand the resolution by a factor of 4 in x-axis, y-axis and z-axis. The feature maps 538 may be fed into a sigmoid function to obtain auxiliary 2 (539).

The feature maps 545 at the second highest resolution layer may be fed into a de-convolutional layer to generate feature maps 548 and expand the resolution from 64×64×12 to 128×128×24 (full resolution). In one embodiment as shown in FIG. 6A, the de-convolutional layer may expand the resolution by a factor of 2 in x-axis, y-axis and z-axis. The feature maps 548 may be fed into a sigmoid function to obtain auxiliary 3 (549).

The one or more auxiliary predictions 529, 539, 549, and 559 in FIG. 6A may be combined together to generate the mask for the tissue or lesion. The manner of combination will be discussed in more detail below.

For example, one implementation for combining the auxiliary predictions 529, 539, 549, and 559 is shown in FIG. 6B. In particular, the auxiliary predictions 529, 539, 549, and 559 may be concatenated together in step 620 to generate a concatenated auxiliary prediction 621. The concatenated auxiliary prediction 621 may have a size of 128×128×24 and a depth of four. The concatenated auxiliary prediction 621 may be fed into a convolutional layer with kernel size of 1×1×1 to generate auxiliary prediction 623. The auxiliary prediction 623 may have a size of 128×128×24 and a depth of one. The auxiliary prediction 623 may be fed into a sigmoid function to obtain final prediction 629.

The final prediction 629 may be used to further determine the mask for the tissue or lesion. During the training process of input images for the FCN model in FIG. 6B, the output segmentation mask generated from the prediction 629 may be compared with the ground truth mask of the input images. A loss function may be determined. In one implementation, the loss function may include a soft max cross-entropy loss. In another implementation, the loss function may include dice coefficient (DC) loss function.

Figure 6C:
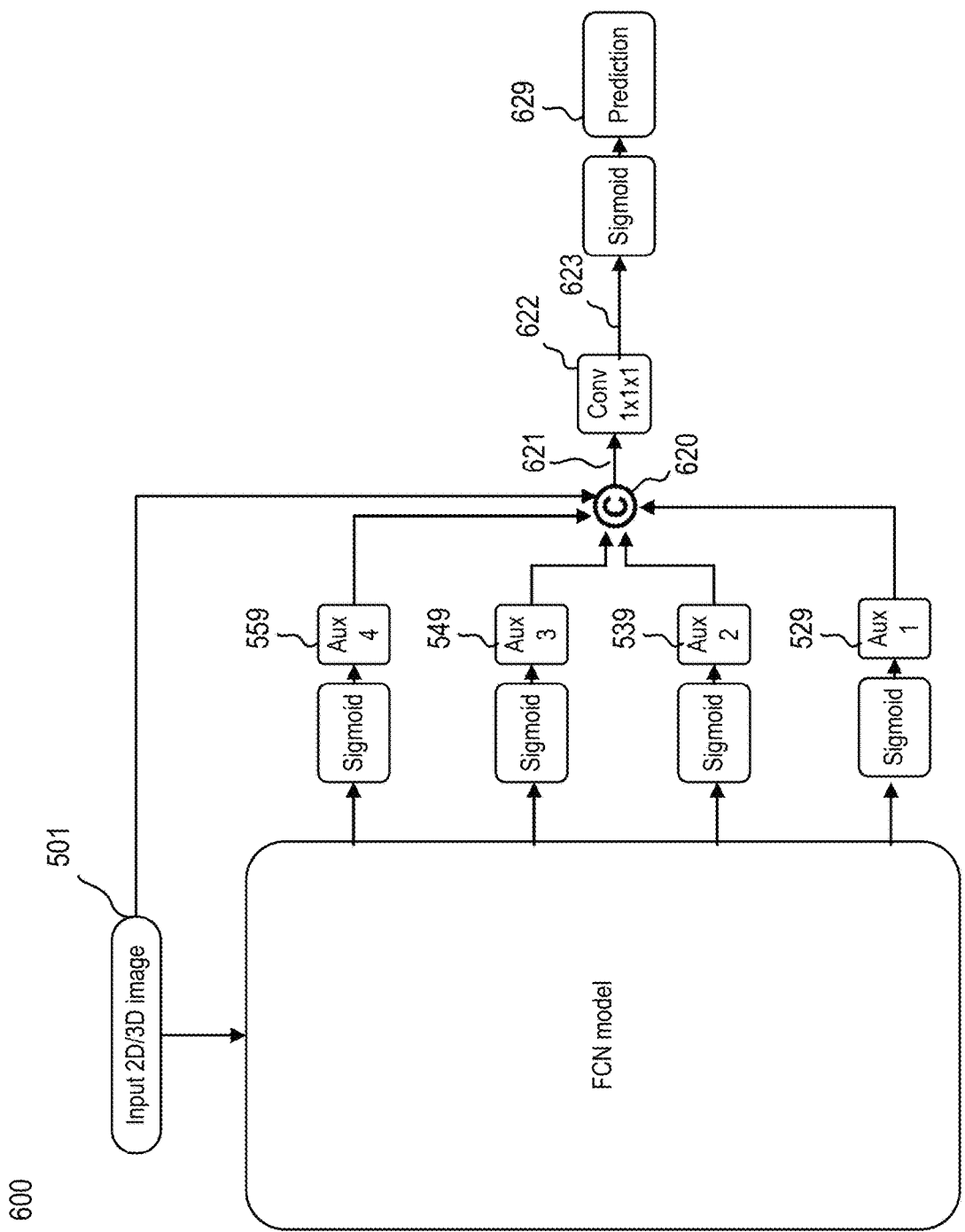
FIG. 6C illustrates an exemplary implementation and data/logic flows of the enhanced fully convolutional neural network of FIG. 6B with further improvement.

The implementation of FIG. 6B may be further augmented as shown in FIG. 6C, where an auto-context strategy may be further used in the FCN model. Specifically, the input 2D/3D images 501 in addition to the auxiliary predictions 529, 539, 549, and 559 may be concatenated together in step 620 to generate a combined auxiliary prediction 621. The concatenated auxiliary prediction 621 may have a size of 128×128×24 and a depth of five (compared with the depth of 4 for the implementation of FIG. 6B). The concatenated auxiliary prediction 621 may be fed into a convolutional layer with kernel size of 1×1×1 to generate auxiliary prediction 623. The auxiliary prediction 623 may have a size of 128×128×24 and a depth of one. The auxiliary prediction 623 may be fed into a sigmoid function to obtain final prediction 629. The final prediction 629 may be used to further determine the mask for the tissue or lesion.

Figure 6D:
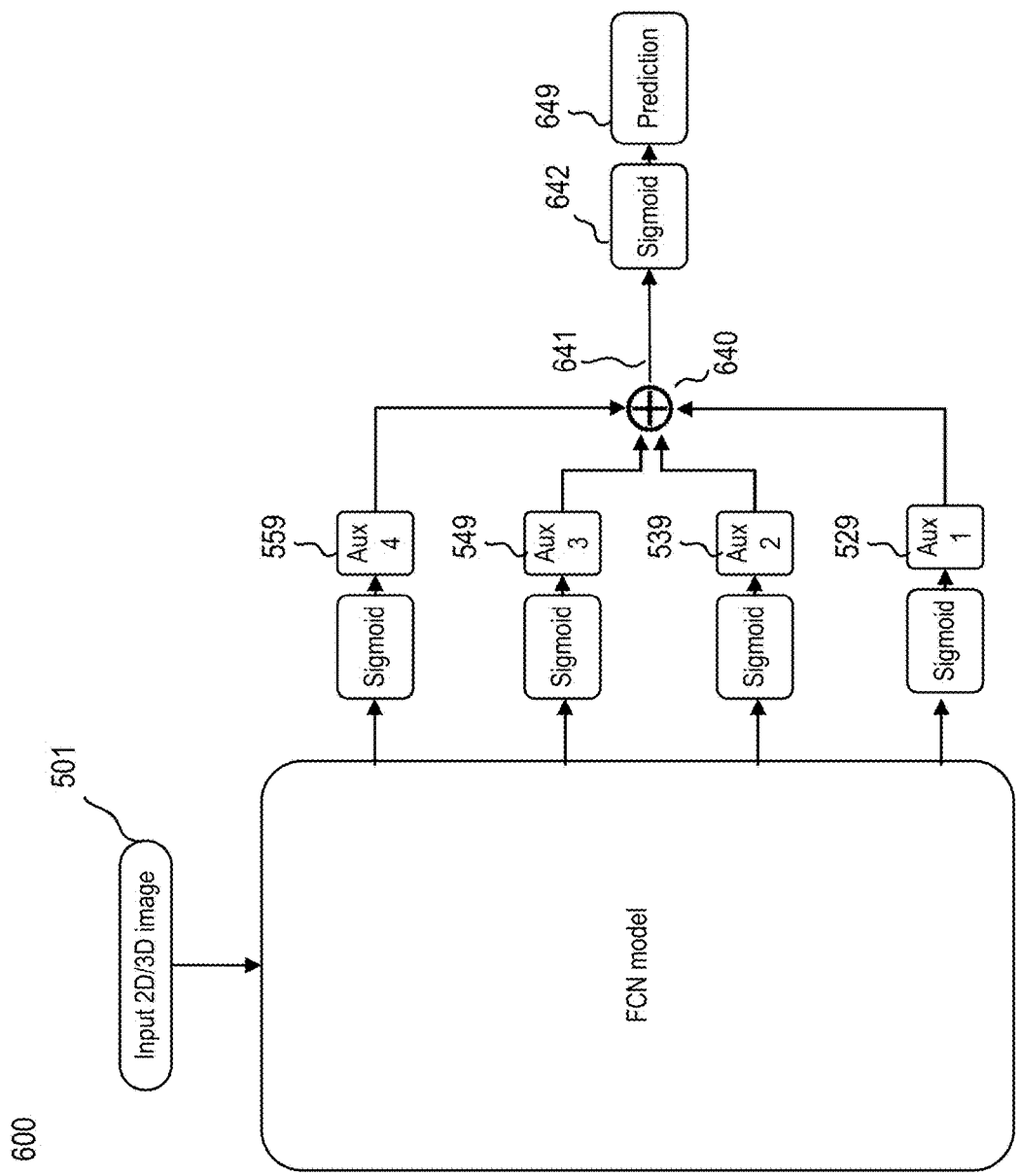
FIG. 6D illustrates an exemplary implementation and data/logic flows of the enhanced fully convolutional neural network of FIG. 6A that combines the auxiliary segmentation masks by summation.

Another implementation for combining auxiliary predictions 529, 539, 549, and 559 is shown in FIG. 6D where an element-by-element summation rather than concatenation is used. Specifically, the auxiliary predictions 529, 539, 549, and 559 may be added together in step 640 element-by-element to generate a combined auxiliary prediction 641. The combined auxiliary prediction 641 may have a size of 128×128×24 and a depth of one. The combined auxiliary prediction 641 may be fed into a sigmoid function 642 to obtain final prediction 649. The final prediction 649 may be used to further determine the mask for the tissue or lesion.

Figure 6E:
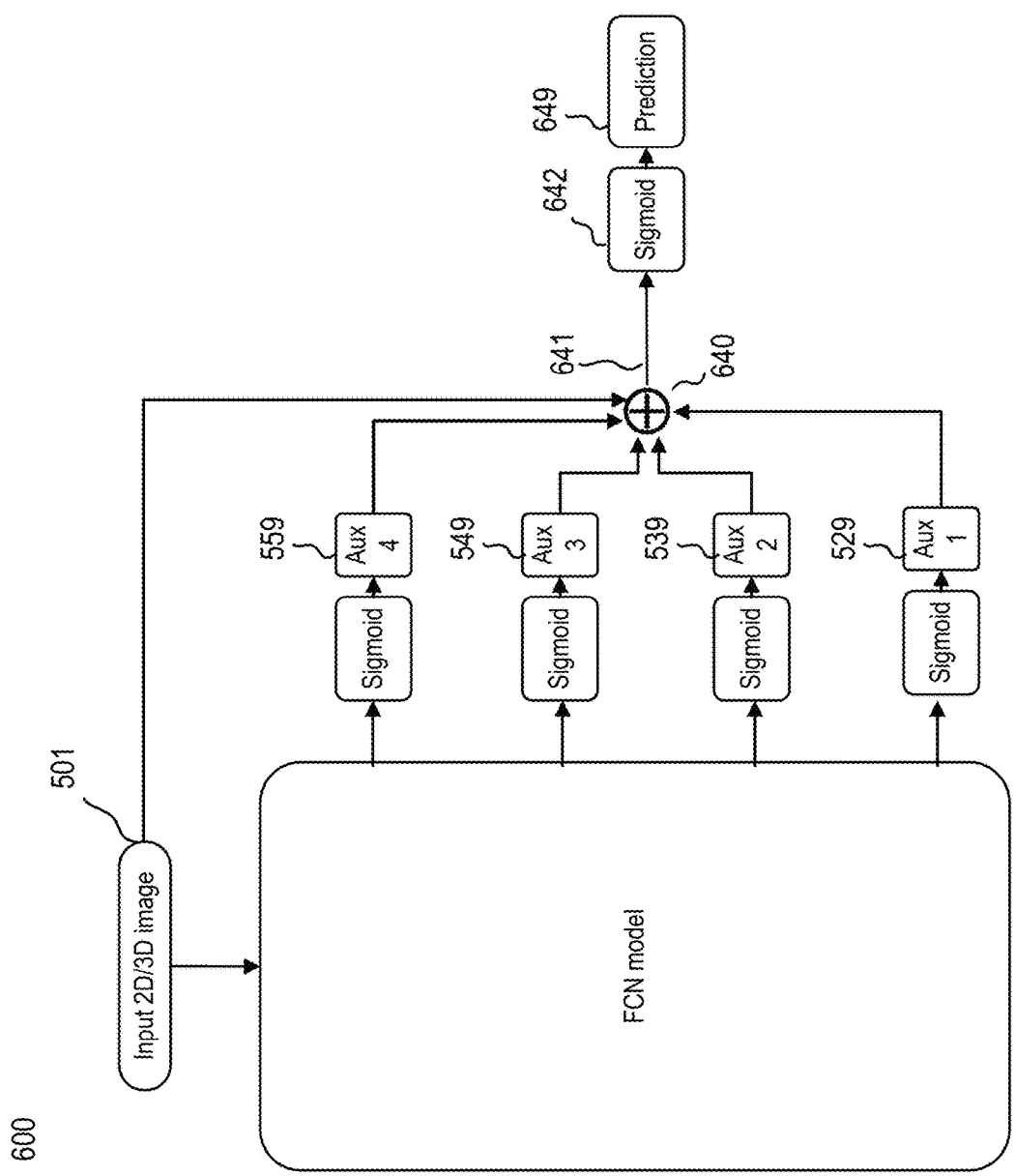
FIG. 6E illustrates an exemplary implementation and data/logic flows of the enhanced fully convolutional neural network of FIG. 6D with further improvement.

The implementation of FIG. 6D may be further augmented as shown in FIG. 6E. Specifically, the input 2D/3D images 501 in addition to the auxiliary predictions 529, 539, 549, and 559 may be added together in step 640 in an element-by-element manner to generate a combined auxiliary prediction 641. The combined auxiliary prediction 641 may have a size of 128×128×24 and a depth of one. The combined auxiliary prediction 641 may be fed into a sigmoid function 642 to obtain final prediction 649. The final prediction 629 may be used to further determine the mask for the tissue or lesion of the input image.

Figure 6F:
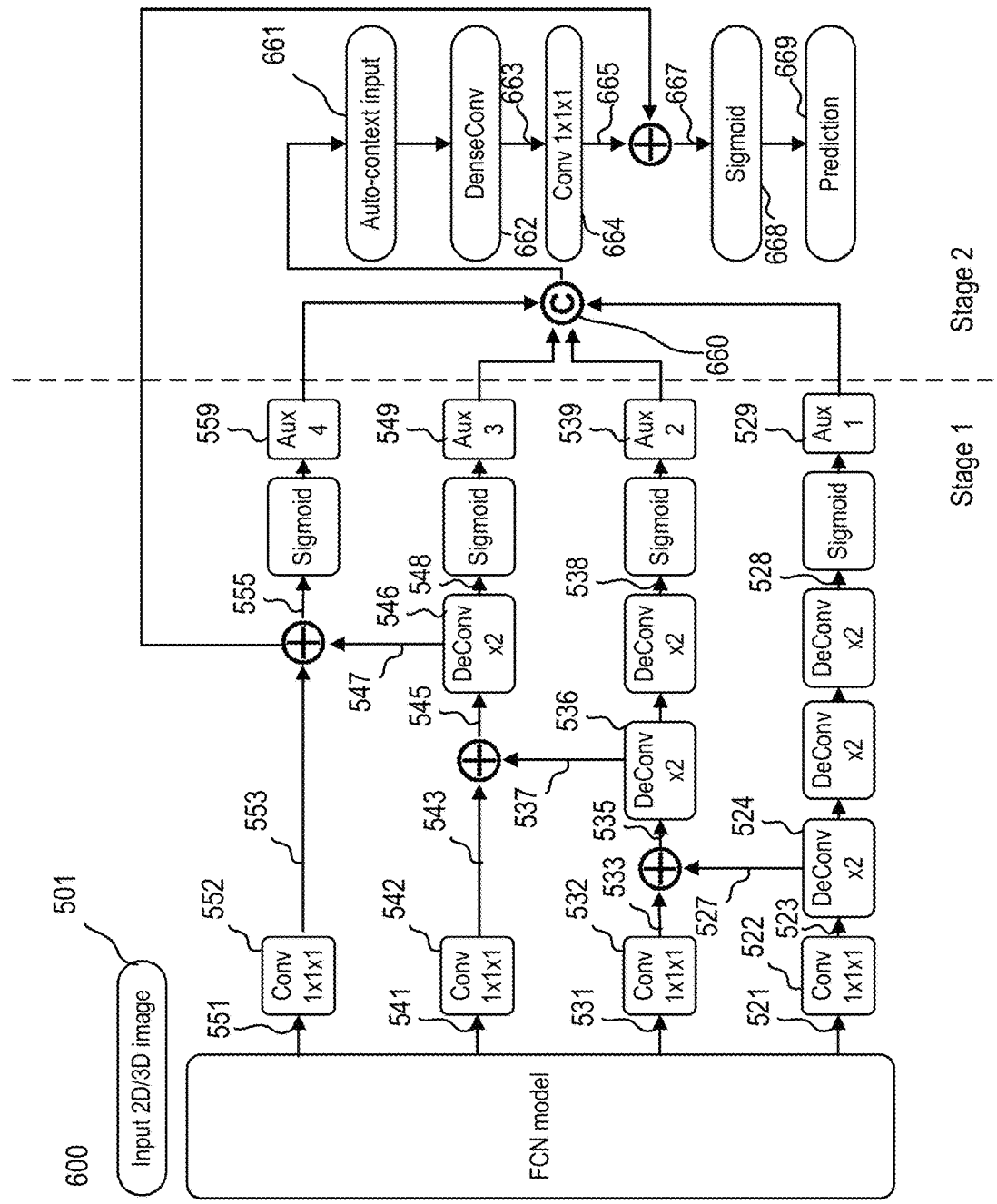
FIG. 6F illustrates an exemplary implementation and data/logic flows of the enhanced fully convolutional neural network of FIG. 6B as stage I, further including a dense-convolution (DenseConv) module in a stage II.

Fully Convolutional Network (FCN) with Coarse-To-Fine Architecture and Densely Connected Convolutional Module Another implementation of the FCN based on FIG. 6A is shown in FIG. 6F, where the combination of the auxiliary prediction masks 529, 539, 549, and 559 may be further processed by a densely connected convolutional (DenseConv) network to extract auto-context features prior to obtaining the final prediction mask 669.

Particularly in FIG. 6F, the auxiliary predictions 529, 539, 549, and 559 may be concatenated together in step 660 to generate a concatenated auxiliary prediction, also referred to as auto-context input 661. The concatenated auxiliary prediction 661 may have a size of 128×128×24 and a depth of four. The auto-context input 661 may be fed into a DenseConv module 662 to generate a prediction map 663. The prediction map 663 may have a depth of one or more. The prediction map 663 may be fed into a convolutional layer 664 to generate a prediction map 665. The prediction map 665 may have a size of 128×128×24 and a depth of one.

The prediction map 665 may be optionally added together with the feature maps 555 in an element-by-element manner to generate a prediction map 667. The prediction map 667 may have a size of 128×128×24 and a depth of one. The prediction map 667 may be fed into a sigmoid function 668 to obtain final prediction 669.

The final prediction 669 may be used to further determine the mask for the tissue or lesion. During the training process of input images for the FCN model in FIG. 6F, the output segmentation mask generated from the prediction 629 may be compared with the ground truth mask of the input images. A loss function may be determined. In one implementation, the loss function may include a soft max cross-entropy loss. In another implementation, the loss function may include dice coefficient (DC) loss function.

Figure 6G:
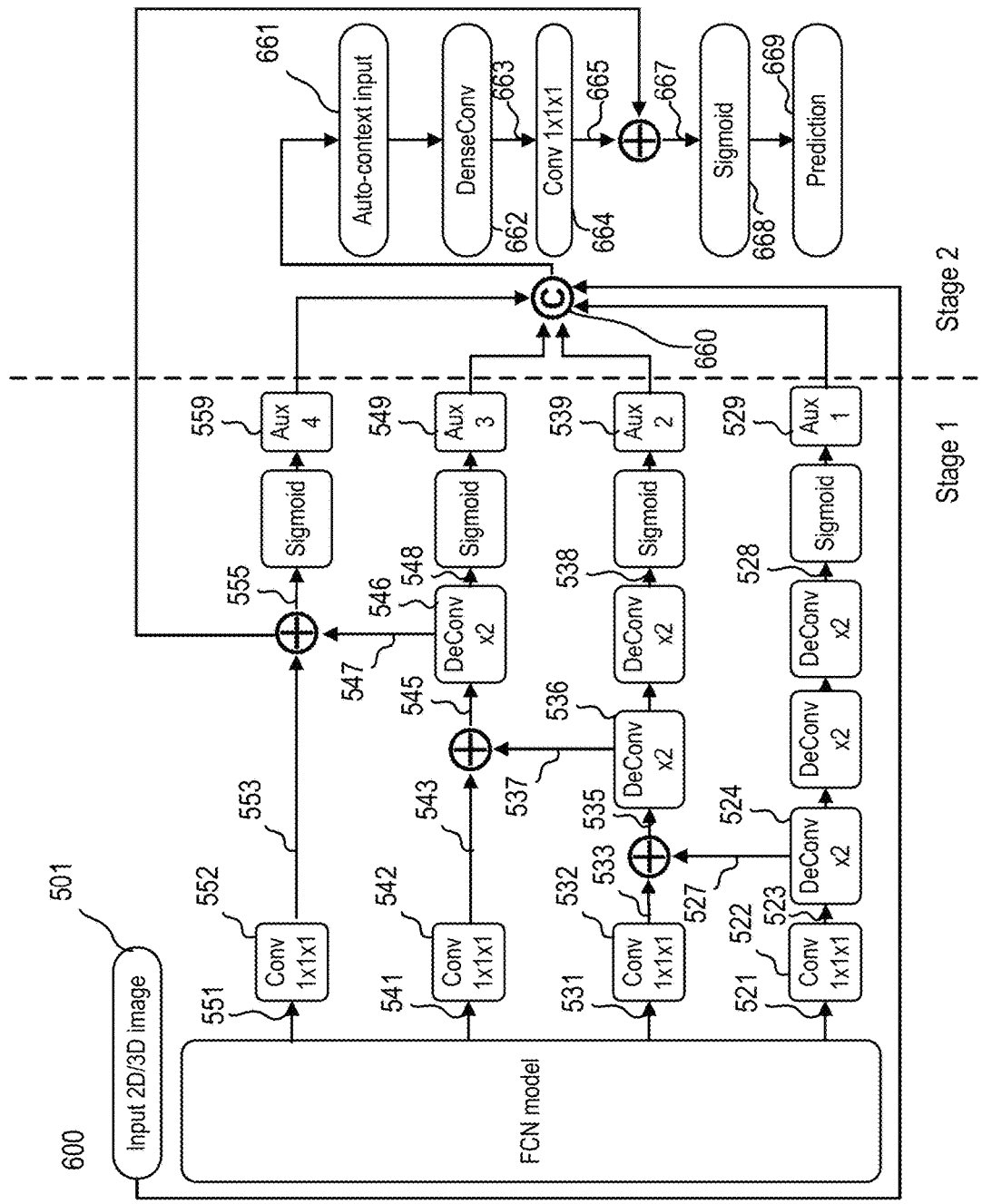
FIG. 6G illustrates an exemplary implementation and data/logic flows of the enhanced fully convolutional neural network of FIG. 6F with further improvement.

The implementation of FIG. 6F may be further augmented as shown in FIG. 6G. In FIG. 6G, the input 2D/3D images 501 in addition to the auxiliary predictions 529, 539, 549, and 559 may be concatenated together in step 660 to generate the auto-context input 661. The concatenated auxiliary input at 661 may have a size of 128×128×24 and a depth of five rather than the depth of 4 in FIG. 6F. The auto-context input 661 may be fed into a DenseConv module 662 to generate a prediction map 663. The prediction map 663 may have a depth of one or more. The prediction map 663 may be fed into a convolutional layer 664 to generate a prediction map 665. The prediction map 665 may have a size of 128×128×24 and a depth of one.

Similar to FIG. 6F, the prediction map 665 in FIG. 6G may be added together with the feature maps 555 in an element-by-element manner to generate a prediction map 667. The prediction map 667 may have a size of 128×128×24 and a depth of one. The prediction map 667 may be fed into a sigmoid function 668 to obtain final prediction 669. The final prediction 669 may be used to further determine the mask for the tissue or lesion. During the training process of input images for the FCN model in FIG. 6G, the output segmentation mask generated from the prediction 629 may be compared with the ground truth mask of the input images. A loss function may be determined. In one implementation, the loss function may include a soft max cross-entropy loss. In another implementation, the loss function may include dice coefficient (DC) loss function.

Figure 7:
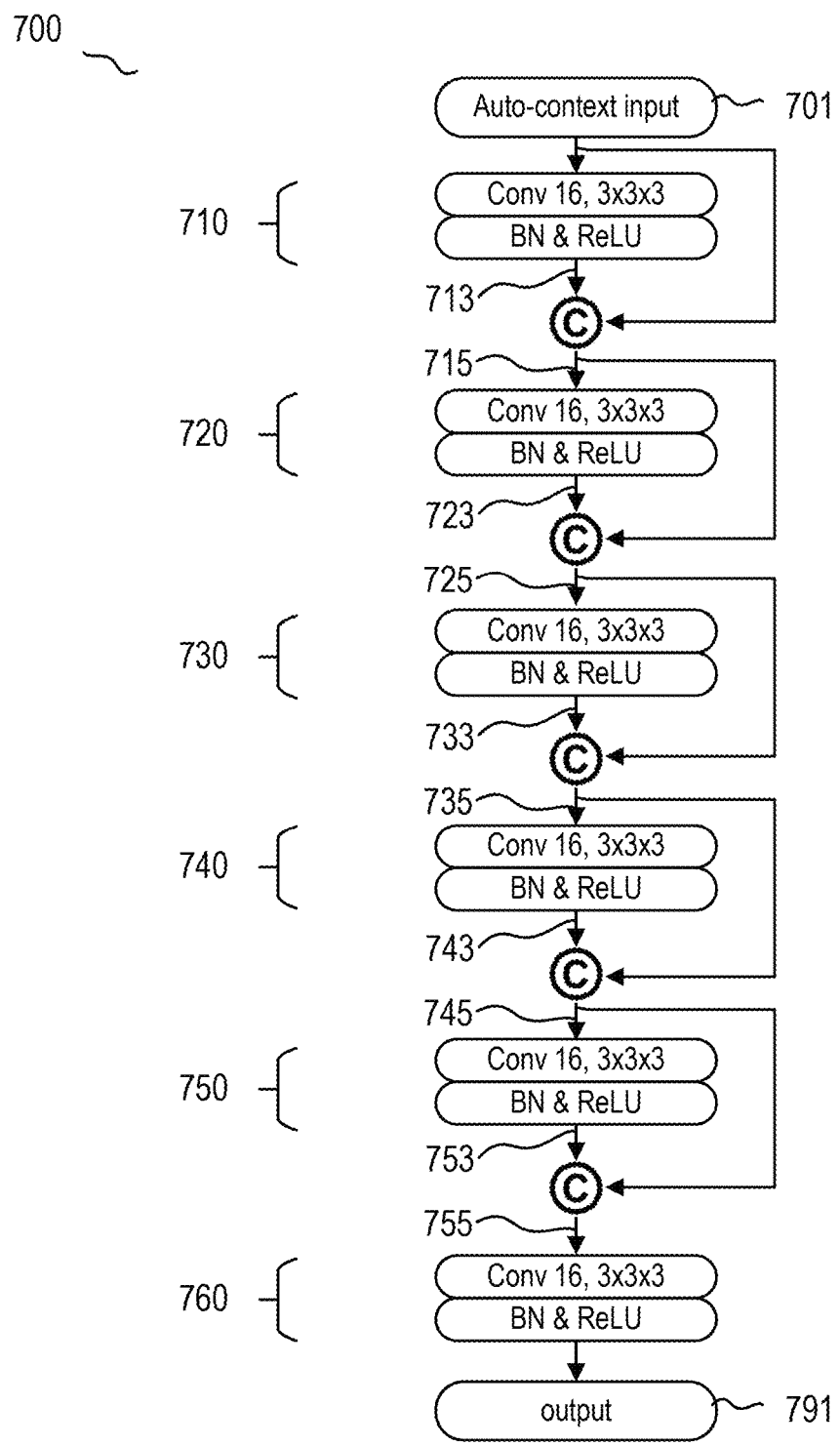
FIG. 7 illustrates an exemplary implementation and data/logic flows of the DenseConv module of FIG. 6F.

The DenseConv module 662 above in FIG. 6F and FIG. 6G may include one or more convolutional layers. One embodiment is shown in FIG. 7 for a DenseConv module 700 including six convolutional layers 710, 720, 730, 740, 750, and 760. Each of the six convolutional layers may include a convolutional layer with an exemplary kernel size 3×3×3 and with a number of feature maps of 16. Each of the six convolution layers may further include a batch normalization (BN) layer, and an ReLU layer.

An auto-context input 701 may be fed into the convolutional layer 710 to generate feature maps 713. In some exemplar implementations, the auto-context input 701 may have a size of 128×128×24 and a depth of four. The feature maps 713 may have a size of 128×128×24 and a depth of 16.

For a current convolutional layer, the input of the current convolutional layer may be concatenated with the output of the current convolutional layer to generate the input for the next convolutional layer.

For example, as shown in FIG. 7, the auto-context input 701 may be concatenated with the output 713 of the convolutional layer 710 to generate the feature maps 715. The feature maps 715 may be the input for the convolutional layer 720.

As shown in FIG. 7, the feature maps 715 may be fed into the convolutional layer 720 to generate the feature maps 723. The feature maps 723 may be concatenated with the feature maps 715 to generate the feature maps 725. The feature maps 725 may be the input for the convolutional layer 730.

As further shown in FIG. 7, the feature maps 725 may be fed into the convolutional layer 730 to generate the feature maps 733. The feature maps 733 may be concatenated with the feature maps 725 to generate the feature maps 735. The feature maps 735 may be the input for the convolutional layer 740. The feature maps 735 may be fed into the convolutional layer 740 to generate the feature maps 743. The feature maps 743 may be concatenated with the feature maps 735 to generate the feature maps 745. The feature maps 745 may be the input for the convolutional layer 750. Furthermore, the feature maps 745 may be fed into the convolutional layer 750 to generate the feature maps 753. The feature maps 753 may be concatenated with the feature maps 745 to generate the feature maps 755. The feature maps 755 may be the input for the convolutional layer 760.

As shown in FIG. 7, the feature maps 755 may be fed into the convolutional layer 760 to generate the feature maps, which serve as the output 791 of the DenseConv module 700.

The six-convolutional layer DenseConv implementation above is merely exemplary. In other embodiment, the DenseConv module 700 may include any number of convolutional layers, and each of the convolutional layers may use any kernel size and/or include any number of features.

Training

During training process, the output segmentation mask generated in forward-propagation from an FCN model may be compared with the ground truth mask of the input images. A loss function may be determined. In one implementation, the loss function may include a soft max cross-entropy loss.

In another implementation, the loss function may include dice coefficient (DC) loss function. Then a back-propagation through the FCN model may be performed based on, e.g., stochastic gradient descent, and aimed at minimizing the loss function. By iterating the forward-propagation and back-propagation for the same input images, and for the entire training image set, the training parameters may converge to provide acceptable errors between the predicted masks and ground truth masks for all or most of the input images. The converged training parameters, including but not limited to the convolutional features/kernels and various weights and bias, may form a final predictive model that may be further verified using test images and used to predict segmentation or lesion masks for images that the network has never seen before. The FCN model is preferably trained to promote errors on the over-inclusive side to reduce or prevent false negatives in later stage of CAD based on a predicted mask.

Figure 8:
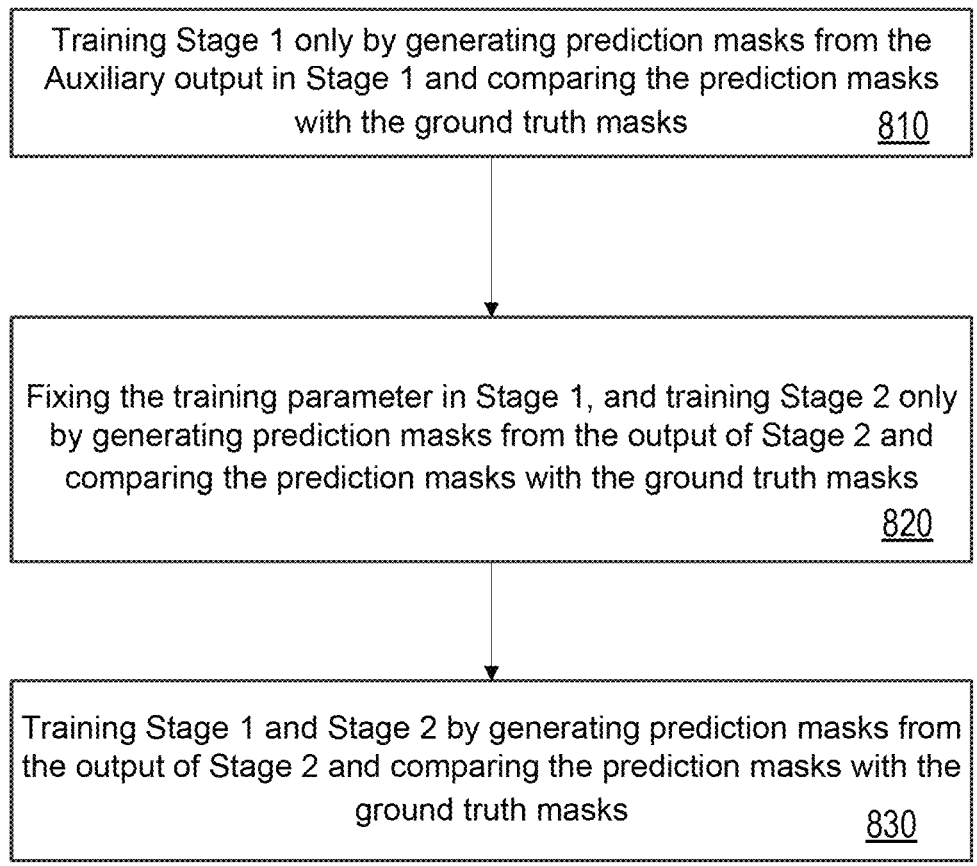
FIG. 8 illustrates a flow diagram of a method for training the exemplary implementation in FIG. 6F or 6G.

For complex models with multiple stages such as the ones shown in FIGS. 6F and 6G including model stage I and stage II, the training process may include three steps as shown in FIG. 8.

Step 810 may include training Stage 1 (of the FCN model, e.g., FIGS. 6F and 6G) for generating prediction masks based on one or more Auxiliary outputs in Stage by comparing the prediction masks with the ground truth masks. The one or more Auxiliary output in Stage 1 may include one or more from the Auxiliary 1-4 (529, 539, 549, and 559).

Step 820 may include fixing the training parameter in Stage 1 and training Stage 2 (of the FCN model, e.g., FIGS. 6F and 6G) by generating prediction masks based on the output of Stage 2 and comparing the prediction masks with the ground truth masks. Stage 2 may include a DenseConv module, and the output of Stage 2 may include Prediction 669.

Step 830 may include fine tuning and training of Stage 1 and Stage 2 jointly by using the model parameters obtained in steps 810 and 820 as initial values and further performing forward and back-propagation training processes based on the output of Stage 2. Stage 2 may include a DenseConv module, and the output of Stage 2 may include Prediction 669.

System with Different FCN Models

Figure 9:
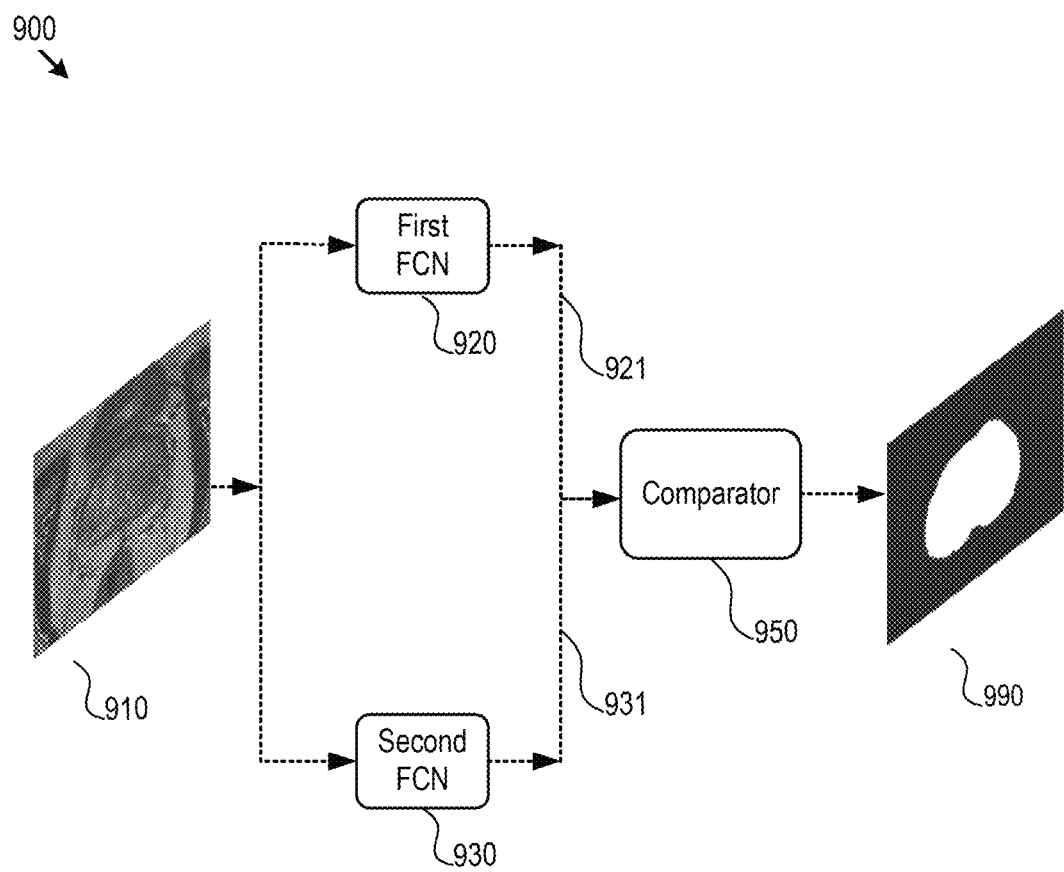
FIG. 9 illustrates an exemplary implementation and data/logic flows of combining various fully convolutional neural networks.

Because different FCN models trained under different conditions may perform well for different input images and under various circumstances, a segmentation/lesion detection model may include multiple FCN sub-models to improve prediction accuracy. FIG. 9 shows one embodiment of a system 900 including two different FCN models: a first FCN 920 and a second FCN 930.

The first FCN 920 and the second FCN 930 may be different in term of their architecture, for example, the first FCN 920 may be an FCN model similar to the model in FIG. 3, and the second FCN 930 may be an FCN model similar the model in FIG. 6F.

The first FCN 920 and the second FCN 930 may be different in term of how the multiple channels are processed, for example, the first FCN 920 may be an FCN model processing each channel individually and independently (e.g., FCN(2D/3D, SC), as described above), and the second FCN 930 may be an FCN model processing all multiple channels together in an aggregated manner (e.g., FCN (2D/3D, MC), as described above).

For input images 910 of the system 900 in FIG. 9, a first predication 921 may be generated from the first FCN 920 and a second prediction 931 may be generated from the second FCN 930. The first predication 921 and second prediction 931 may be fed into a parameterized comparator 950 to determine which prediction of 921 and 931 to select, so as to generate a final prediction 990. The parameters for the comparator may be trained.

The selection by the comparator 950 may be performed at an individual pixel/voxel level, i.e., the comparator 950 may select, for each individual pixel/voxel, which probability for the corresponding pixel/voxel, out of the first predication 921 and second prediction 931, as the final prediction for the corresponding pixel/voxel.

Hardware Implementations

Figure 10:
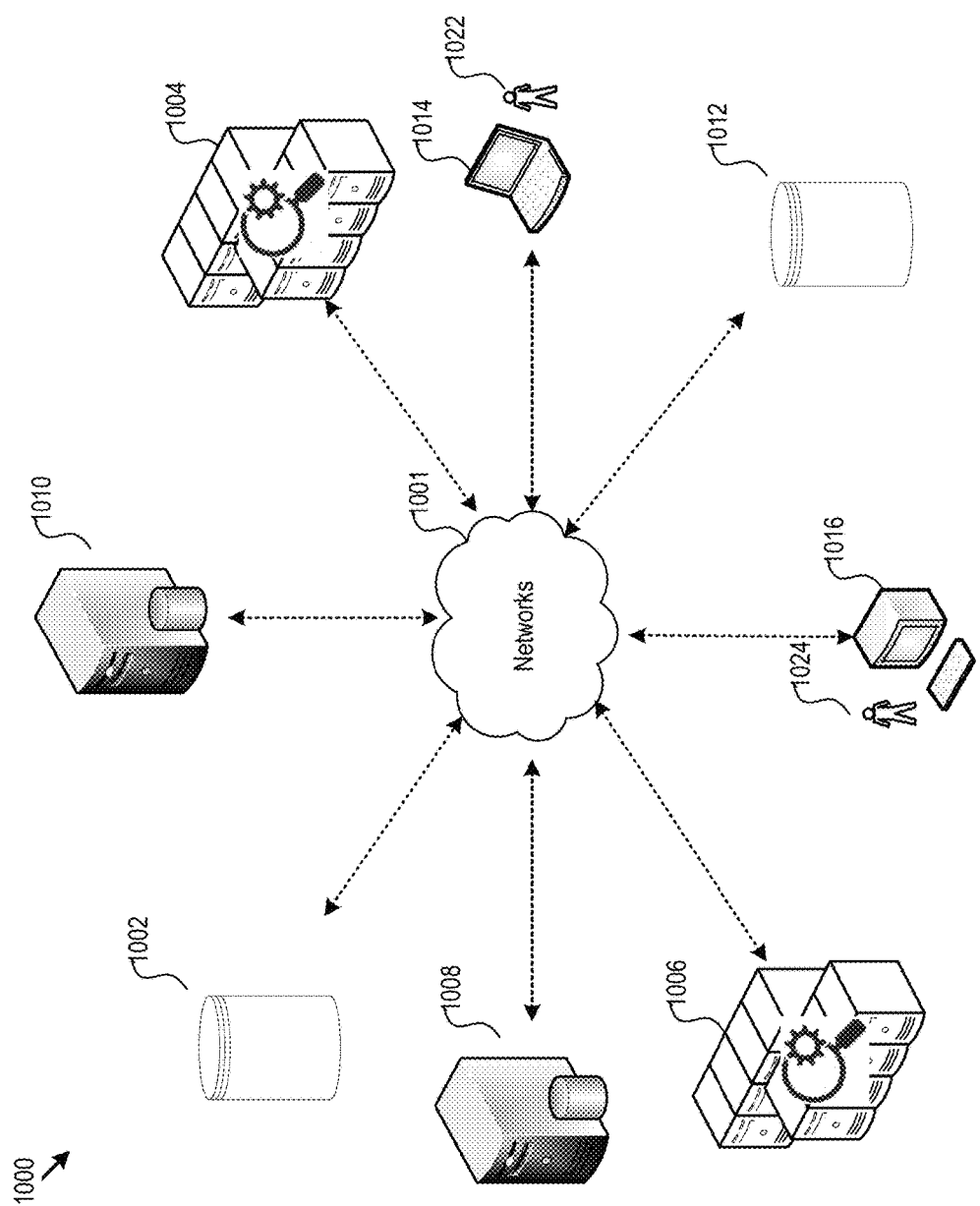
FIG. 10 shows an exemplary computer platform for segmenting digital images.

The FCN image segmentation and/or lesion detection above may be implemented as a computer platform 1000 shown in FIG. 10. The computer platform 1000 may include one or more training servers 1004 and 1006, one or more prediction engines 1008 and 1010, one or more databases 1012, one or more model repositories 1002, and user devices 1014 and 1016 associated with users 1022 and 1024. These components of the computer platform 1000 are inter-connected and in communication with one another via public or private communication networks 1001.

The training servers and prediction engine 1004, 1006, 1008, and 1010 may be implemented as a central server or a plurality of servers distributed in the communication networks. The training servers 1004 and 1006 may be responsible for training the FCN segmentation model discussed above. The prediction engine 1008 and 1010 may be responsible to analyze an input image using the FCN segmentation model to generate a segmentation mask for the input image. While the various servers are shown in FIG. 10 as implemented as separate servers, they may be alternatively combined in a single server or single group of distributed servers combining the functionality of training and prediction. The user devices 1014 and 1016 may be of any form of mobile or fixed electronic devices including but not limited to desktop personal computer, laptop computers, tablets, mobile phones, personal digital assistants, and the like. The user devices 1014 and 1016 may be installed with a user interface for accessing the digital platform.

The one or more databases 1012 of FIG. 10 may be hosted in a central database server or a plurality of distributed database servers. For example, the one or more databases 1020 may be implemented as being hosted virtually in a cloud by a cloud service provider. The one or more databases 1020 may organize data in any form, including but not limited to relational database containing data tables, graphic database containing nodes and relationships, and the like. The one or more databases 1020 may be configured to store, for example, images and their labeled masks collected from various sources. These images and labels may be used as training data corpus for the training server 1006 for generating DCNN segmentation models.

The one or more model repositories 602 may be used to store, for example, the segmentation model with its trained parameters. In some implementation, the model repository 602 may be integrated as part of the predictive engines 608 and 601.

Figure 11:
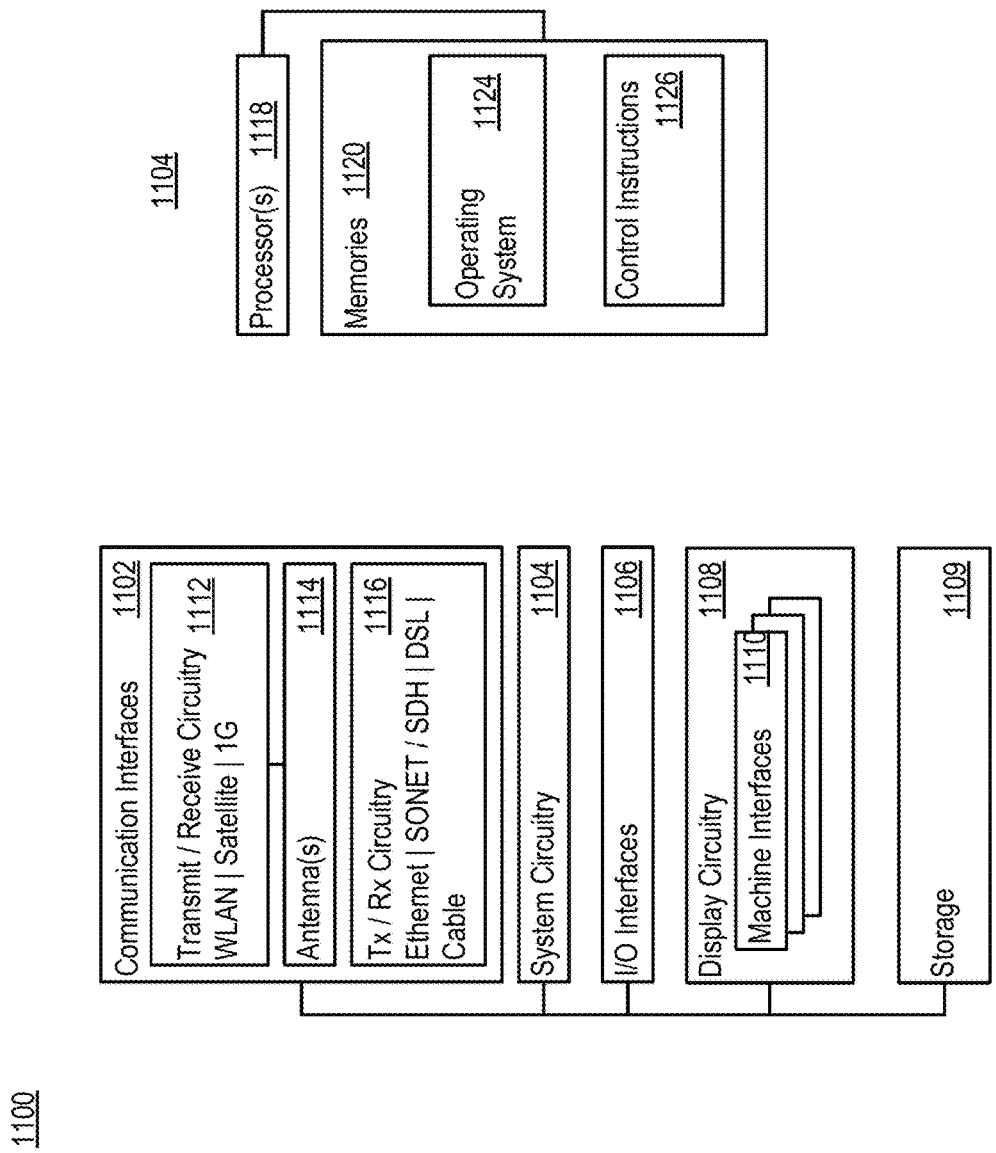
FIG. 11 illustrates a computer system that may be used to implement various computing components and functionalities of the computer platform of FIG. 10.

FIG. 11 shows an exemplary computer system 1100 for implementing any of the computing components of FIGS. 1-10. The computer system 1100 may include communication interfaces 1102, system circuitry 1104, input/output (I/O) interfaces 1106, storage 1109, and display circuitry 1108 that generates machine interfaces 1110 locally or for remote display, e.g., in a web browser running on a local or remote machine. The machine interfaces 1110 and the I/O interfaces 1106 may include GUIs, touch sensitive displays, voice or facial recognition inputs, buttons, switches, speakers and other user interface elements. Additional examples of the I/O interfaces 1106 include microphones, video and still image cameras, headset and microphone input/output jacks, Universal Serial Bus (USB) connectors, memory card slots, and other types of inputs. The I/O interfaces 1106 may further include magnetic or optical media interfaces (e.g., a CDROM or DVD drive), serial and parallel bus interfaces, and keyboard and mouse interfaces.

The communication interfaces 1102 may include wireless transmitters and receivers ("transceivers") 1112 and any antennas 1114 used by the transmitting and receiving circuitry of the transceivers 1112. The transceivers 1112 and antennas 1114 may support Wi-Fi network communications, for instance, under any version of IEEE 802.11, e.g., 802.11n or 802.11ac. The communication interfaces 1102 may also include wireline transceivers 1116. The wireline transceivers 1116 may provide physical layer interfaces for any of a wide range of communication protocols, such as any type of Ethernet, data over cable service interface specification (DOCSIS), digital subscriber line (DSL), Synchronous Optical Network (SONET), or other protocol.

The storage 1109 may be used to store various initial, intermediate, or final data or model needed for the implantation of the computer platform 1000. The storage 1109 may be separate or integrated with the one or more databases 1012 of FIG. 10. The storage 1109 may be centralized or distributed, and may be local or remote to the computer system 1100. For example, the storage 1109 may be hosted remotely by a cloud computing service provider.

The system circuitry 1104 may include hardware, software, firmware, or other circuitry in any combination. The system circuitry 1104 may be implemented, for example, with one or more systems on a chip (SoC), application specific integrated circuits (ASIC), microprocessors, discrete analog and digital circuits, and other circuitry. The system circuitry 1104 is part of the implementation of any desired functionality related to the reconfigurable computer platform 1000. As just one example, the system circuitry 1104 may include one or more instruction processors 1118 and memories 1120. The memories 1120 stores, for example, control instructions 1126 and an operating system 1124. In one implementation, the instruction processors 1118 executes the control instructions 1126 and the operating system 1124 to carry out any desired functionality related to the reconfigurable computer platform 1000.

The methods, devices, processing, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

While the particular invention has been described with reference to illustrative embodiments, this description is not meant to be limiting. Various modifications of the illustrative embodiments and additional embodiments of the invention will be apparent to one of ordinary skill in the art from this description. Those skilled in the art will readily recognize that these and various other modifications can be made to the exemplary embodiments, illustrated and described herein, without departing from the spirit and scope of the present invention. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

What is claimed is:

1. A method for image segmentation, comprising:
receiving, by a computer comprising a memory storing instructions and a processor in communication with the memory, a set of training images labeled with a corresponding set of ground truth segmentation masks;
establishing, by the computer, a fully convolutional neural network comprising a multi-layer contraction convolutional neural network and an expansion convolutional neural network connected in tandem; and
iteratively training, by the computer, the full convolution neural network in an end-to-end manner using the set of training images and the corresponding set of ground truth segmentation masks by:
down-sampling a training image of the set of training images through the multi-layer contraction convolutional neural network to generate an intermediate feature map, wherein a resolution of the intermediate feature map is lower than a resolution of the training image;
up-sampling the intermediate feature map through the multi-layer expansion convolutional neural network to generate a first feature map and a second feature map, wherein a resolution of the second feature map is larger than the resolution of the first feature map;

generating, based on the first feature map and the second feature map, with resolution adjustment, a predictive segmentation mask for the training image;

generating an end loss based on a difference between the predictive segmentation mask and a ground truth segmentation mask corresponding to the training image;

back-propagating the end loss through the full convolutional neural network; and minimizing the end loss by adjusting a set of training parameters of the fully convolutional neural network using gradient descent.

2. The method of claim 1, wherein the generating, by the computer based on the first feature map and the second feature map, with resolution adjustment, the predictive segmentation mask for the training image comprises:

implementing, by the computer, a first auxiliary convolutional layer on the first feature map to generate a convoluted first feature map, the convoluted first feature map having a same resolution as the first feature map, the convoluted first feature map having a depth of one;

implementing, by the computer, a second auxiliary convolutional layer on the second feature map to generate a convoluted second feature map, the convoluted second feature map having a same resolution as the second feature map, the convoluted second feature map having a depth of one; and generating, by the computer based on the convoluted first feature map and the convoluted second feature map, with resolution adjustment, the predictive segmentation mask for the training image.

3. The method of claim 2, wherein the generating, by the computer based on the convoluted first feature map and the convoluted second feature map, the predictive segmentation mask for the training image comprises:

implementing, by the computer, a first de-convolutional layer on the convoluted first feature map to generate a de-convoluted first feature map, the de-convoluted first feature map having a larger resolution than the first feature map; and generating, by the computer based on the de-convoluted first feature map and the convoluted second feature map, the predictive segmentation mask for the training image.

4. The method of claim 3, wherein:

the de-convoluted first feature map has a same resolution as the convoluted second feature map; and the generating, by the computer based on the de-convoluted first feature map and the convoluted second feature map, the predictive segmentation mask for the training image comprises:

concatenating, by the computer, the de-convoluted first feature map and the convoluted second feature map to generate a concatenated second feature map, and generating, by the computer based on the concatenated second feature map, the predictive segmentation mask for the training image.

5. The method of claim 4, wherein the generating, by the computer based on the concatenated second feature map, the predictive segmentation mask for the training image comprises:

performing, by the computer, a second sigmoid function on the concatenated second feature map to generate a second auxiliary prediction map; and generating, by the computer based on the second auxiliary prediction map, the predictive segmentation mask for the training image.

6. The method of claim 5, wherein the generating, by the computer based on the concatenated second feature map, the predictive segmentation mask for the training image comprises:

performing, by the computer, a first sigmoid function on the de-convoluted first feature map to generate a first auxiliary prediction map;

concatenating, by the computer, the first auxiliary prediction map and the second auxiliary prediction map to generate an auto-context prediction map;

generating, by the computer based on the auto-context prediction map, the predictive segmentation mask for the training image.

7. The method of claim 6, wherein the concatenating, by the computer, the first auxiliary prediction map and the second auxiliary prediction map to generate the auto-context prediction map comprises:

concatenating, by the computer, the training image, the first auxiliary prediction map, and the second auxiliary prediction map to generate the auto-context prediction map.

8. The method of claim 7, wherein the generating, by the computer based on the auto-context prediction map, the predictive segmentation mask for the training image comprises:

performing, by the computer, a densely connected convolutional (DenseConv) operation on the auto-context prediction map to generate a DenseConv prediction map, the DenseConv operation including one or more convolutional layers; and generating, by the computer based on the DenseConv prediction map, the predictive segmentation mask for the training image.

9. The method of claim 8, wherein the generating, by the computer based on the DenseConv prediction map, the predictive segmentation mask for the training image comprises:

performing, by the computer, a DenseConv auxiliary convolutional layer on the DenseConv prediction map to generate a convoluted DenseConv prediction map;

concatenating, by the computer, the convoluted DenseConv prediction map and the concatenated second feature map to generate the concatenated DenseConv prediction map; and generating, by the computer based on the concatenated DenseConv prediction map, the predictive segmentation mask for the training image.

10. The method of claim 9, further comprising:

determining, by the computer, whether the training image is a three-dimensional image; and in response to determining that the training image is the three-dimensional image:

setting, by the computer, the first auxiliary convolutional layer to have a kernel size of 1×1×1, setting, by the computer, the second auxiliary convolutional layer to have a kernel size of 1×1×1, and setting, by the computer, the DenseConv auxiliary convolutional layer to have a kernel size of 1×1×1.

11. The method of claim 2, further comprising:

storing, by the computer, the iteratively trained fully convolutional neural network with the set of training parameters in a predictive model repository;

receiving, by the computer, an input image, wherein the input image comprises one of a test image or a unlabeled image; and forward-propagating, by the computer, the input image through the iteratively trained fully convolutional neural network with the set of training parameters to generate an output segmentation mask.

12. A computer image segmentation system for digital images, comprising:
a communication interface circuitry;
a database;
a predictive model repository; and
a processing circuitry in communication with the database and the predictive model repository, the processing circuitry configured to:
receive a set of training images labeled with a corresponding set of ground truth segmentation masks;
establish a fully convolutional neural network comprising a multi-layer contraction convolutional neural network and an expansion convolutional neural network connected in tandem; and
iteratively train the full convolution neural network in an end-to-end manner using the set of training images and the corresponding set of ground truth segmentation masks by configuring the processing circuitry to:
down-sample a training image of the set of training images through the multi-layer contraction convolutional neural network to generate an intermediate feature map, wherein a resolution of the intermediate feature map is lower than a resolution of the training image,
up-sample the intermediate feature map through the multi-layer expansion convolutional neural network to generate a first feature map and a second feature map, wherein a resolution of the second feature map is larger than the resolution of the first feature map,
generate, based on the first feature map and the second feature map, with resolution adjustment, a predictive segmentation mask for the training image,
generate, based on a loss function, an end loss based on a difference between the predictive segmentation mask and a ground truth segmentation mask corresponding to the training image,
back-propagating, by the computer, the end loss through the full convolutional neural network, and
minimizing, by the computer, the end loss by adjusting a set of training parameters of the fully convolutional neural network using gradient descent.

13. The computer image segmentation system of claim 12, wherein when the processing circuitry is configured to generate, based on the first feature map and the second feature map, with resolution adjustment, the predictive segmentation mask for the training image, the processing circuitry is configured to:
perform a first auxiliary convolutional layer on the first feature map to generate a convoluted first feature map, the convoluted first feature map having a same resolution as the first feature map, the convoluted first feature map having a depth of one;
perform a second auxiliary convolutional layer on the second feature map to generate a convoluted second feature map, the convoluted second feature map having a same resolution as the second feature map, the convoluted second feature map having a depth of one; and
generate, based on the convoluted first feature map and the convoluted second feature map, with resolution adjustment, the predictive segmentation mask for the training image.

14. The computer image segmentation system of claim 13, wherein when the processing circuitry is configured to generate, based on the convoluted first feature map and the convoluted second feature map, with resolution adjustment, the predictive segmentation mask for the training image, the processing circuitry is configured to:
perform a first de-convolutional layer on the convoluted first feature map to generate a de-convoluted first feature map, the de-convoluted first feature map having a larger resolution than the first feature map; and
generate, based on the de-convoluted first feature map and the convoluted second feature map, the predictive segmentation mask for the training image.

15. The computer image segmentation system of claim 14, wherein:
the de-convoluted first feature map having a same resolution as the convoluted second feature map; and
when the processing circuitry is configured to generate, based on the de-convoluted first feature map and the convoluted second feature map, the predictive segmentation mask for the training image, the processing circuitry is configured to:
concatenate the de-convoluted first feature map and the convoluted second feature map to generate a concatenated second feature map, and
generate, based on the concatenated second feature map, the predictive segmentation mask for the training image.

16. The computer image segmentation system of claim 15, wherein when the processing circuitry is configured to generate, based on the concatenated second feature map, the predictive segmentation mask for the training image, the processing circuitry is configured to:
perform a first sigmoid function on the de-convoluted first feature map to generate a first auxiliary prediction map;
perform a second sigmoid function on the concatenated second feature map to generate a second auxiliary prediction map; and
concatenate the training image, the first auxiliary prediction map, and the second auxiliary prediction map to generate an auto-context prediction map;
generate, based on the auto-context prediction map, the predictive segmentation mask for the training image.

17. The computer image segmentation system of claim 16, wherein when the processing circuitry is configured to generate, based on the auto-context prediction map, the predictive segmentation mask for the training image, the processing circuitry is configured to:
perform a densely connected convolutional (DenseConv) operation on the auto-context prediction map to generate a DenseConv prediction map, the DenseConv operation including one or more convolutional layers; and
perform a DenseConv auxiliary convolutional layer on the DenseConv prediction map to generate a convoluted DenseConv prediction map;
concatenate the convoluted DenseConv prediction map and the concatenated second feature map to generate the concatenated DenseConv prediction map; and generate, based on the concatenated DenseConv prediction map, the predictive segmentation mask for the training image.

18. The computer image segmentation system of claim 12, wherein the processing circuitry is further configured to:
store the iteratively trained fully convolutional neural network with the set of training parameters in a predictive model repository;
receive an input image, wherein the input image comprises one of a test image or a unlabeled image; and
forward-propagate the input image through the iteratively trained fully convolutional neural network with the set of training parameters to generate an output segmentation mask.

19. A non-transitory computer readable storage medium storing instructions, wherein the instructions, when executed by a processor, cause the processor to:
receive a set of training images labeled with a corresponding set of ground truth segmentation masks;
establish a fully convolutional neural network comprising a multi-layer contraction convolutional neural network and an expansion convolutional neural network connected in tandem; and
iteratively train the full convolution neural network in an end-to-end manner using the set of training images and the corresponding set of ground truth segmentation masks by causing the processor to:
down-sample a training image of the set of training images through the multi-layer contraction convolutional neural network to generate a intermediate feature map, wherein a resolution of the intermediate feature map is lower than a resolution of the training image,
up-sample the intermediate feature map through the multi-layer expansion convolutional neural network to generate a first feature map and a second feature map, wherein a resolution of the second feature map is larger than the resolution of the first feature map,
generate, based on the first feature map and the second feature map, with resolution adjustment, a predictive segmentation mask for the training image,
generate, based on a loss function, an end loss based on a difference between the predictive segmentation mask and a ground truth segmentation mask corresponding to the training image,
back-propagate the end loss through the full convolutional neural network, and
minimize the end loss by adjusting a set of training parameters of the fully convolutional neural network using gradient descent.

20. The non-transitory computer readable storage medium according to claim 19, wherein, when the instructions cause the processor to generate, based on the first feature map and the second feature map, with resolution adjustment, the predictive segmentation mask for the training image, the instructions cause the processor to:
perform a first auxiliary convolutional layer on the first feature map to generate a convoluted first feature map, the convoluted first feature map having a same resolution as the first feature map, the convoluted first feature map having a depth of one;
perform a second auxiliary convolutional layer on the second feature map to generate a convoluted second feature map, the convoluted second feature map having a same resolution as the second feature map, the convoluted second feature map having a depth of one;
perform a first de-convolutional layer on the convoluted first feature map to generate a de-convoluted first feature map, the de-convoluted first feature map having a larger resolution than the first feature map;
concatenate the de-convoluted first feature map and the convoluted second feature map to generate a concatenated second feature map;
perform a first sigmoid function on the de-convoluted first feature map to generate a first auxiliary prediction map;
perform a second sigmoid function on the concatenated second feature map to generate a second auxiliary prediction map;
concatenate the training image, the first auxiliary prediction map, and the second auxiliary prediction map to generate an auto-context prediction map;
perform a densely connected convolutional (DenseConv) operation on the auto-context prediction map to generate a DenseConv prediction map, the DenseConv operation including one or more convolutional layers;
perform a DenseConv auxiliary convolutional layer on the DenseConv prediction map to generate a convoluted DenseConv prediction map;
concatenate the convoluted DenseConv prediction map and the concatenated second feature map to generate the concatenated DenseConv prediction map; and
generate, based on the concatenated DenseConv prediction map, the predictive segmentation mask for the training image.

21. The non-transitory computer readable storage medium according to claim 19, wherein the instructions, when executed by a processor, further cause the processor to:
store the iteratively trained fully convolutional neural network with the set of training parameters in a predictive model repository;
receive an input image, wherein the input image comprises one of a test image or a unlabeled image; and
forward-propagate the input image through the iteratively trained fully convolutional neural network with the set of training parameters to generate an output segmentation mask.

* * * * *